United States Patent
Hanakawa et al.

(10) Patent No.: US 9,387,346 B2
(45) Date of Patent: Jul. 12, 2016

(54) PARTICLE BEAM TREATMENT SYSTEM AND BEAM POSITION CORRECTING METHOD THEREOF

(71) Applicant: Mitsubishi Electric Corporation, Chiyoda-ku (JP)

(72) Inventors: Kazushi Hanakawa, Chiyoda-ku (JP); Kengo Sugahara, Chiyoda-ku (JP); Shuhei Odawara, Chiyoda-ku (JP); Hisashi Harada, Chiyoda-ku (JP); Masahiro Ikeda, Chiyoda-ku (JP); Toshihiro Otani, Chiyoda-ku (JP); Taizo Honda, Chiyoda-ku (JP); Katsuhisa Yoshida, Chiyoda-ku (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 4 days.

(21) Appl. No.: 14/346,908

(22) PCT Filed: Sep. 21, 2012

(86) PCT No.: PCT/JP2012/074222
§ 371 (c)(1),
(2) Date: Mar. 24, 2014

(87) PCT Pub. No.: WO2013/069379
PCT Pub. Date: May 16, 2013

(65) Prior Publication Data
US 2014/0235922 A1   Aug. 21, 2014

(30) Foreign Application Priority Data
Nov. 8, 2011 (WO) .................. PCT/JP2011/075683

(51) Int. Cl.
*A61N 5/10* (2006.01)
*H05H 7/04* (2006.01)

(52) U.S. Cl.
CPC ............ *A61N 5/1042* (2013.01); *A61N 5/1043* (2013.01); *A61N 5/1067* (2013.01); *H05H 7/04* (2013.01); *A61N 2005/1087* (2013.01); *H05H 2007/048* (2013.01); *H05H 2277/11* (2013.01)

(58) Field of Classification Search
USPC ....................................... 250/492.1
See application file for complete search history.

(56) References Cited

U.S. PATENT DOCUMENTS 6,218,675 B1 *  4/2001  Akiyama et al. ........... 250/492.3
6,639,234 B1 * 10/2003  Badura et al. .............. 250/492.3
(Continued)

FOREIGN PATENT DOCUMENTS

EP     1 348 465 A1   10/2003
EP     1348465 A1    10/2003
(Continued)

OTHER PUBLICATIONS

Extended European Search Report issued on Apr. 28, 2015, by the European Patent Office in corresponding European Patent Application 12848652.9-1652. (6 pages).
(Continued)

*Primary Examiner* — Phillip A Johnston
(74) *Attorney, Agent, or Firm* — Buchanan Ingersoll & Rooney PC

(57) ABSTRACT

A particle beam treatment system includes an accelerator system that accelerates a charged particle beam and a beam transport system that transports a high-energy beam emitted from the accelerator to an irradiation location, wherein the beam transport system is provided with at least one steering electromagnet and at least one beam position monitor corresponding to the at least one steering electromagnet, and wherein the at least one beam position monitor supplies an excitation current for correcting a beam position, which periodically varies, to the at least one steering electromagnet.

8 Claims, 22 Drawing Sheets

(56) References Cited

U.S. PATENT DOCUMENTS

| | | | |
|---|---|---|---|
| 6,774,383 B2* | 8/2004 | Norimine | A61N 5/1048 250/492.3 |
| 2003/0183779 A1 | 10/2003 | Norimine et al. | |
| 2004/0232356 A1 | 11/2004 | Norimine et al. | |
| 2005/0247890 A1 | 11/2005 | Norimine et al. | |
| 2009/0039256 A1* | 2/2009 | Fujii | A61N 5/1048 250/306 |

FOREIGN PATENT DOCUMENTS

| | | |
|---|---|---|
| JP | 2003-282300 A | 10/2003 |
| JP | 2009-000347 A | 1/2009 |
| JP | 2011-130859 A | 7/2011 |
| JP | 2011-206237 A | 10/2011 |

OTHER PUBLICATIONS

International Search Report (PCT/ISA/210) mailed on Nov. 13, 2012, by the Japanese Patent Office as the International Searching Authority for International Application No. PCT/JP2012/074222.

Office Action (Notification of Reasons for Refusal) issued on Oct. 28, 2014, by the Japanese Patent Office in corresponding Japanese Patent Application No. 2013-542890, and a partial English translation of the Office Action. (7 pages).

Taiwan Office Action dated May 19, 2015 issued in corresponding Taiwan Patent Appln. No. 101141099, with partial English translation (7 pages).

* cited by examiner

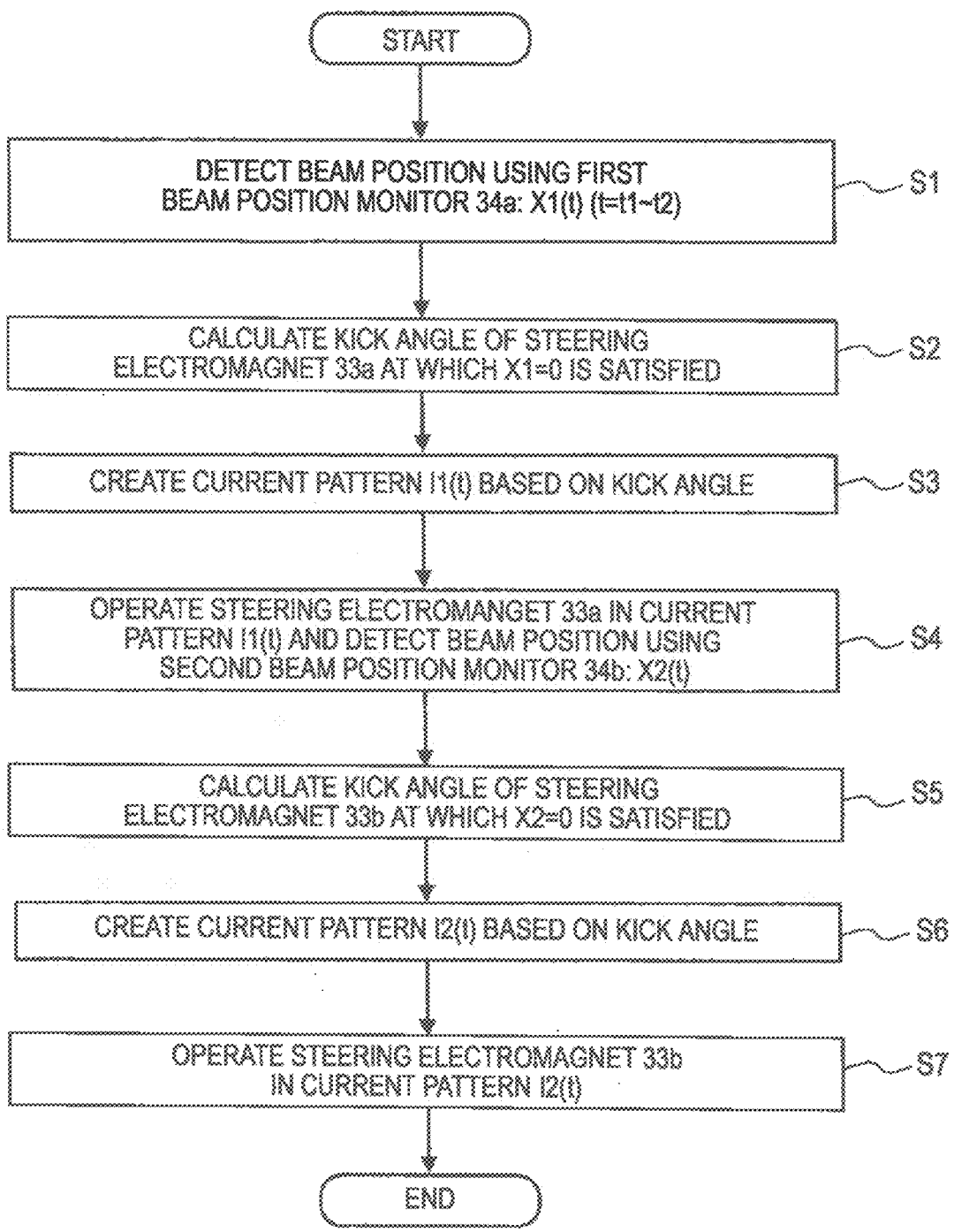

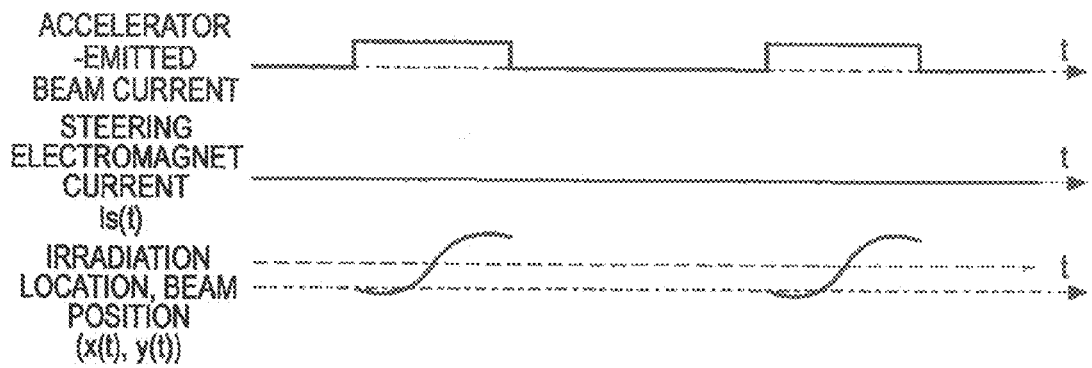
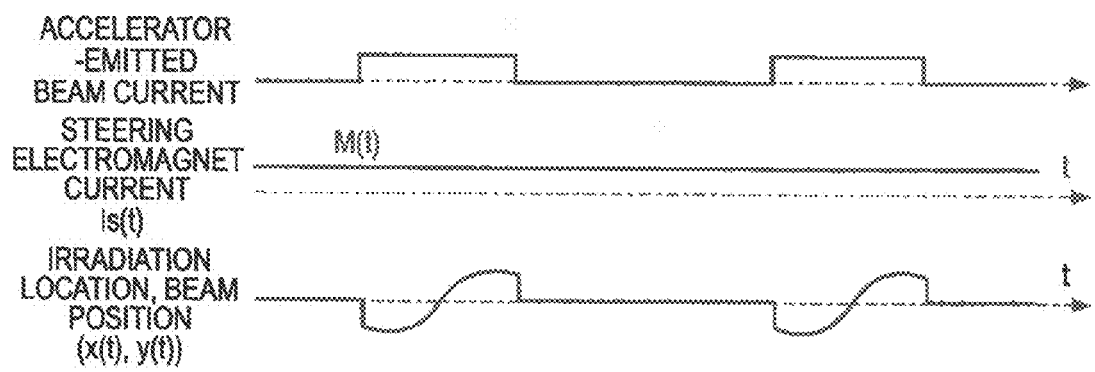
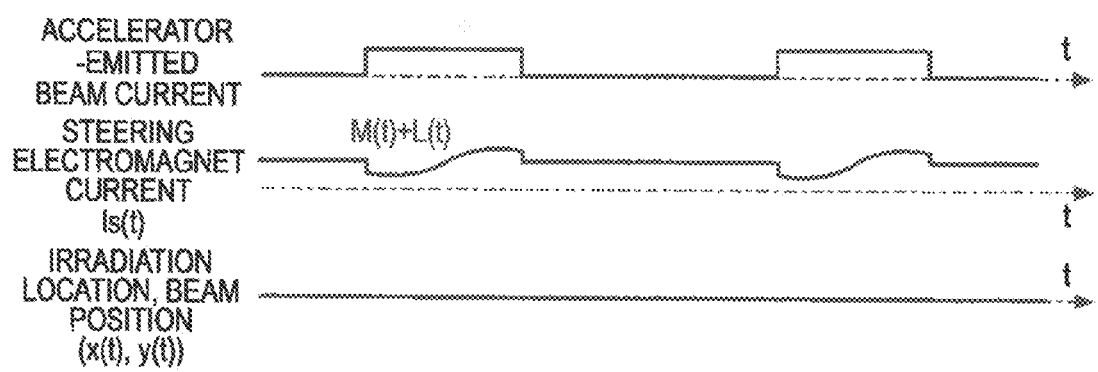

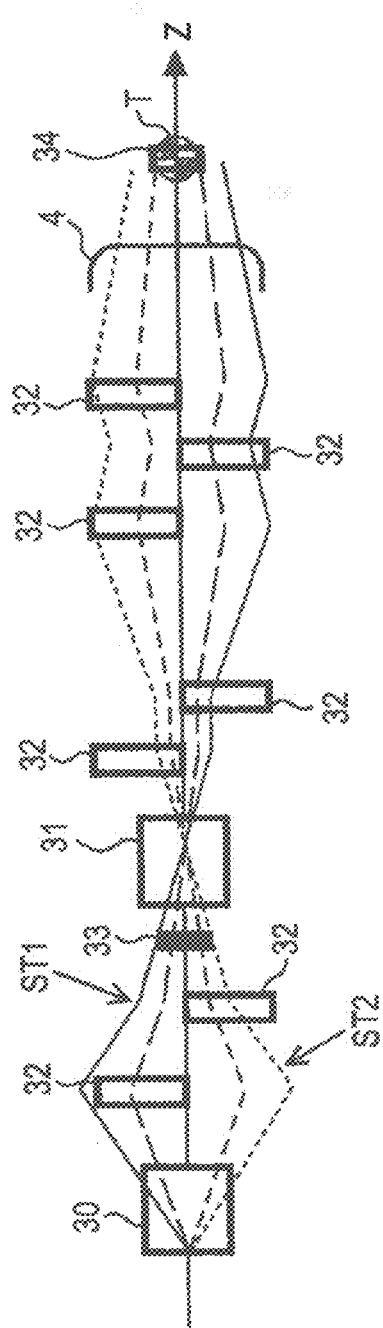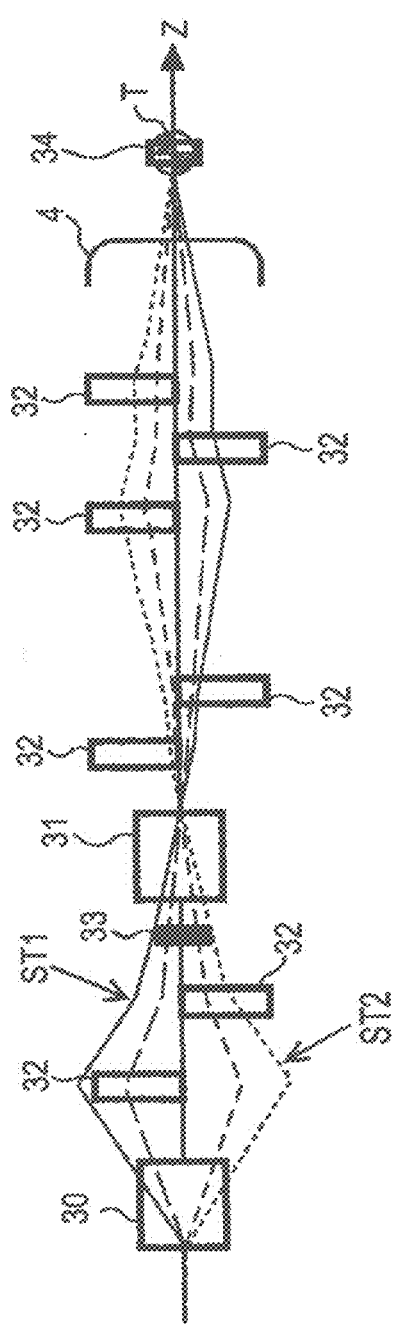
FIG. 11A
FIG. 11B

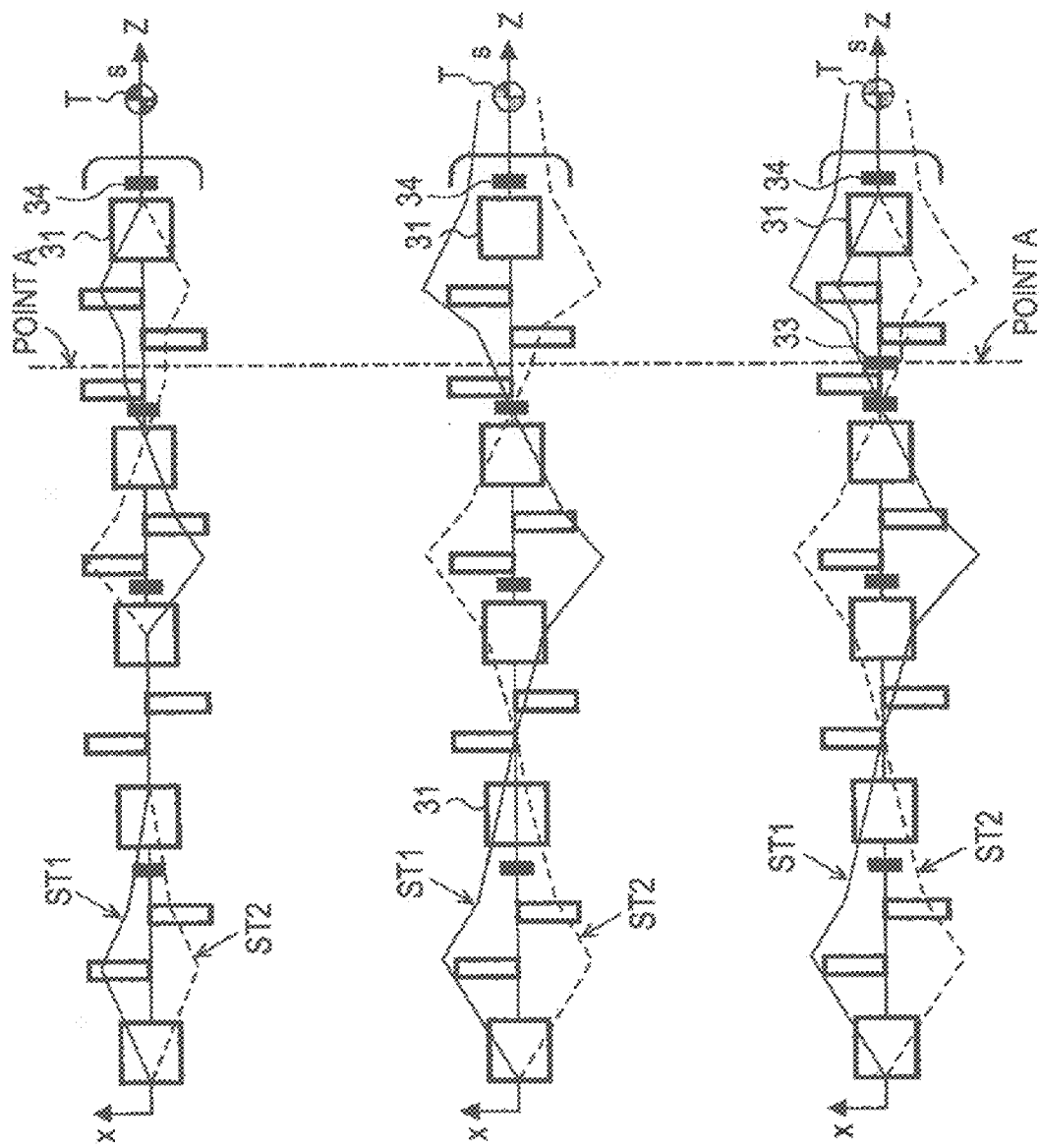

(a)

(b)

PARTICLE BEAM TREATMENT SYSTEM AND BEAM POSITION CORRECTING METHOD THEREOF

TECHNICAL FIELD

The present invention relates to a particle beam treatment system for irradiating an affected part of a cancer with a charged particle beam of protons, carbon, or the like to treat the affected part, and more particularly, to correction of a beam position in a particle beam treatment system using a scanning irradiation (scanning) method.

BACKGROUND ART

Methods of forming an irradiation field in a particle beam treatment system are approximately classified into a broad-beam irradiation method of enlarging a beam by the use of scattering substances and concurrently irradiating the whole affected part of a patient as an irradiation target with the enlarged beam and a scanning irradiation method (scanning method) of directly scanning and irradiating an affected part with a narrow beam by the use of an electromagnet. In any case, since the position and the angle (slope) of a charged particle beam emitted from an accelerator are not stabilized, it is necessary to install beam axis adjusting means including various electromagnets in an irradiation device disposed near a patient or in a beam transport path extending to the irradiation device. However, in the broad-beam irradiation method, since the scattering substances are used, a slight variation of a beam axis has a relatively small influence and thus high-accuracy beam axis correcting means is not necessary. In the scanning irradiation method, since a variation of a beam axis in the beam transport system has an influence on an irradiation field to an affected part, high-accuracy beam axis correcting means is necessary.

Accordingly, as the beam axis correcting method in the scanning irradiation method, for example, a correction method in which a scanning electromagnet and a beam position detector are disposed in an irradiation device, a beam position at a target irradiation location is calculated on the basis of a signal from the beam position detector, and the scanning electromagnet is controlled so as to irradiate the target irradiation location with a scanning beam was proposed in the past (for example, see Patent Literature 1). The scanning electromagnet includes two scanning electromagnets for controlling a beam, which travels in the z direction, independently in the x direction and the y direction, an excitation current based on the signal from the beam position detector is made to flow in the electromagnets, and magnetic fields generated in the respective electromagnets are temporally changed to scan the x direction and the y direction with the beam.

In addition, a method was also proposed in which beam transport means for transporting a charged particle beam emitted from an accelerator to an irradiation device is provided with two beam position detecting means and two steering electromagnets, a displacement is calculated on the basis of detection signals output from the respective beam position detecting means, and excitation currents of the steering electromagnets are controlled on the basis of the displacement (for example, see Patent Literature 2).

However, both methods are directed to implementing a predetermined beam trajectory by feeding back a signal, which is calculated on the basis of the detection signal of the beam position detecting means, as an excitation current of the electromagnet in some way and have a structural problem in that the time delay in a control system due to the feedback affects correction accuracy. When a periodic variation is present in a magnetic field of an electromagnet or high-frequency power in the accelerator at the time of taking out a charged particle beam from the accelerator, a position variation or an angle variation of an emitted beam due to the periodic variation is complicatedly affected and thus it is not possible to suppress the position variation or the angle variation of the emitted beam with satisfactory accuracy using only the conventional beam trajectory adjusting means based on the feedback.

Patent Literature 1: JP-A-2009-000347
Patent Literature 2: JP-A-2003-282300

DISCLOSURE OF INVENTION

Technical Problem

The present invention is made to reduce an influence of such periodic variation factors and an object thereof is to provide a novel particle beam treatment system which can correct an influence on a position variation or an angle variation of an emitted beam in a feed-forward manner by observing the periodic variation by the use of a beam position detecting device and causing a steering electromagnet to generate an excitation pattern for correction and a correction method thereof.

Solution to Problem

According to an aspect of the present invention, there is provided a particle beam treatment system including: an accelerator system that accelerates a charged particle beam; and a beam transport system that transports a high-energy beam emitted from the accelerator system to an irradiation location, wherein the beam transport system is provided with at least one steering electromagnet and at least one beam position monitor corresponding to the at least one steering electromagnet, and wherein the at least one beam position monitor supplies an excitation current for correcting a beam position, which periodically varies, to the at least one steering electromagnet.

According to another aspect of the present invention, there is provided a beam position correcting method of a particle beam treatment system in which a beam transport system is provided with at least one steering electromagnet and at least one beam position monitor corresponding to the at least one steering electromagnet, including: detecting a periodic variation of a beam position by applying a beam in a state where the at least one beam position monitor is detachably disposed at an irradiation location in test irradiation; supplying a value of an excitation current to the at least one steering electromagnet in synchronization with the periodic position variation so as to cancel the periodic variation; acquiring and storing a value of the periodic excitation current; and supplying the periodic excitation current to the at least one steering electromagnet in a state where the at least one beam position monitor is detached from the irradiation location in actual irradiation.

Advantageous Effects of Invention

The particle beam treatment system according to the present invention can more efficiently and satisfactorily improve accuracy of an irradiation location of a charged particle beam by correcting a periodic position variation or a periodic angle variation of an emitted beam in a feed-forward manner.

BRIEF DESCRIPTION OF DRAWINGS

FIG. 4 is a flowchart illustrating a beam correcting procedure using a steering electromagnet power supply in Embodiment 1.

FIG. 6 is a functional block diagram illustrating a beam trajectory correction control state including a corrected current pattern based on a periodic variation factor and a corrected current pattern based on a device arrangement error or the like.

FIGS. 7A to 7C are characteristic diagrams illustrating a state where an effect of the beam trajectory correction control varies depending on the correcting procedure.

FIGS. 11A and 11B are diagrams schematically illustrating a beam trajectory control state in Embodiment 2.

FIGS. 14A to 14C are diagrams schematically illustrating another beam trajectory control method in a preliminary stage of a particle beam treatment system according to Embodiment 4 of the present invention.

BEST MODE FOR CARRYING OUT THE INVENTION

Embodiment 1

Figure 1:
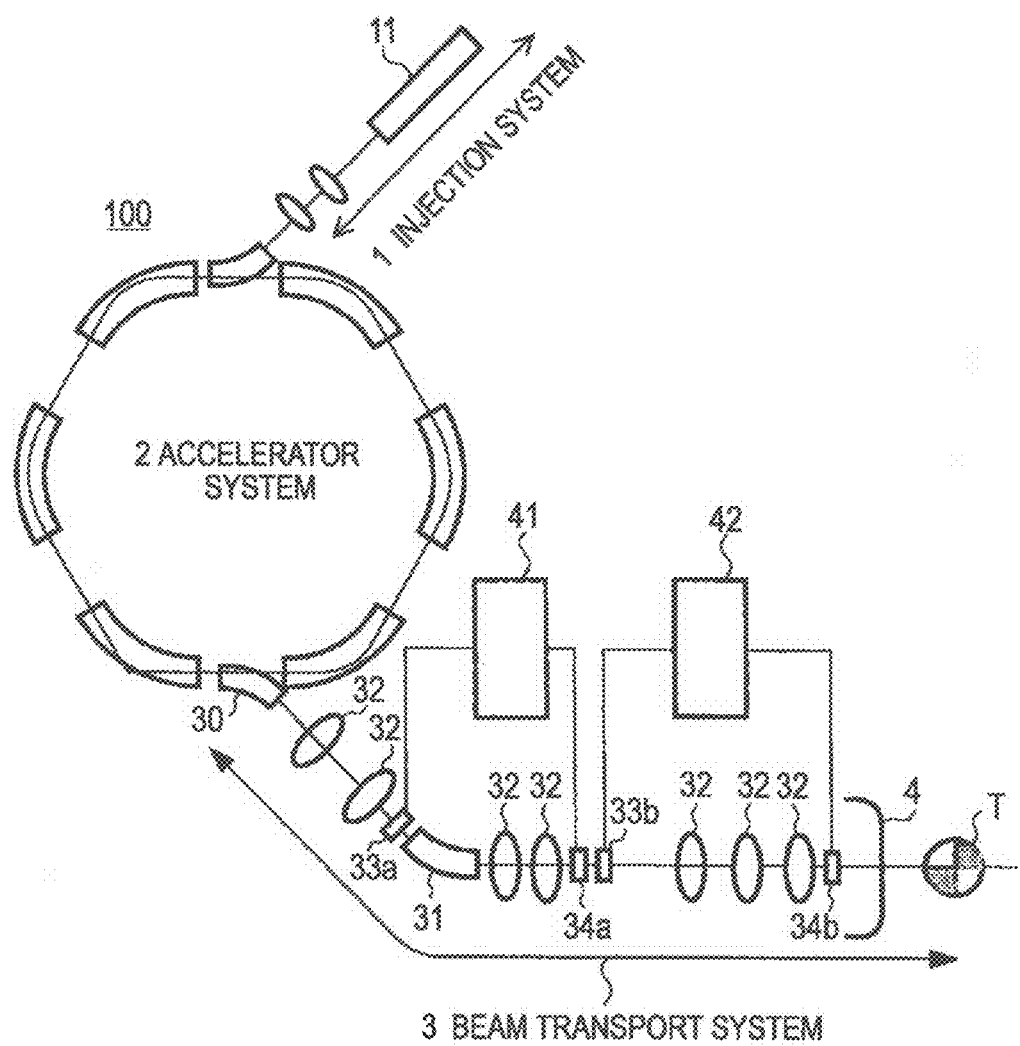
FIG. 1 is a diagram schematically illustrating a configuration of a particle beam treatment system according to Embodiment 1 of the present invention.

A schematic configuration of a particle beam treatment system 100 according to Embodiment 1 of the present invention will be described below with reference to FIG. 1. The particle beam treatment system 100 according to this embodiment includes an injection system 1 that includes an ion source (not illustrated) or an injector 11, an accelerator system 2 such as a synchrotron that accelerates a charged particle beam emitted from the injector 11 to be a beam with necessary energy by circulating the charged particle beam, and a beam transport system 3 that transports the energy beam accelerated by the synchrotron 2 to an irradiation device T in the vicinity of a patient.

In FIG. 1, a charged particle beam generated by the injector 11 is incident on the accelerator system 2 such as a synchrotron, is accelerated to have necessary beam energy thereby, is emitted from an emitting deflection electromagnet 30 to the beam transport system 3, is adjusted in beam trajectory via various electromagnets, and is applied to an irradiation object at an irradiation location T. The beam transport system 3 is provided with a four-pole electromagnet 32 for adjusting a beam size, steering electromagnets 33a and 33b for correcting a beam trajectory, and a deflection electromagnet 31 for deflecting a beam direction. The excitation currents of the steering electromagnets 33a and 33b are controlled by steering electromagnet power supplies 41 and 42, respectively, and an energy beam reaches the irradiation object via a predetermined beam trajectory in the beam transport system.

The beam transport system is provided with two beam position monitors 34a and 34b at predetermined positions on a beam axis. The beam position monitors 34a and 34b employ, for example, a fluorescent plate monitors, and are configured to be freely attached to and detached from the beam path. Reference numerals 41 and 42 represent power supplies for the steering electromagnets 33a and 33b, and include a controller that calculates values of correcting excitation currents of the steering electromagnets 33a and 33b on the basis of the detected values of the beam position in the beam position monitors 34a and 34b and that stores the calculated values.

The number of steering electromagnets 33a and 33b may be at least one and two or more steering electromagnets may be provided if necessary. Each of the two steering electromagnets 33a and 33b described herein includes an x-axis steering electromagnet and a y-axis steering electromagnet particularly working in the x direction and the y direction which are perpendicular to each other and perpendicular to a traveling direction Z of a beam, but the respective steering electromagnets are illustrated as a single part in the drawing. The irradiation with an ion beam from the synchrotron 2 is intermittently performed at predetermined time intervals until reaching at least an energy level necessary for treatment, and an ON/OFF control operation thereof is performed by a high-frequency acceleration cavity (not illustrated) disposed in an orbit of the synchrotron. The ON/OFF period is referred to as an emission period and the ON period thereof is referred to as a beam spill to be provided for treatment.

Figure 2:
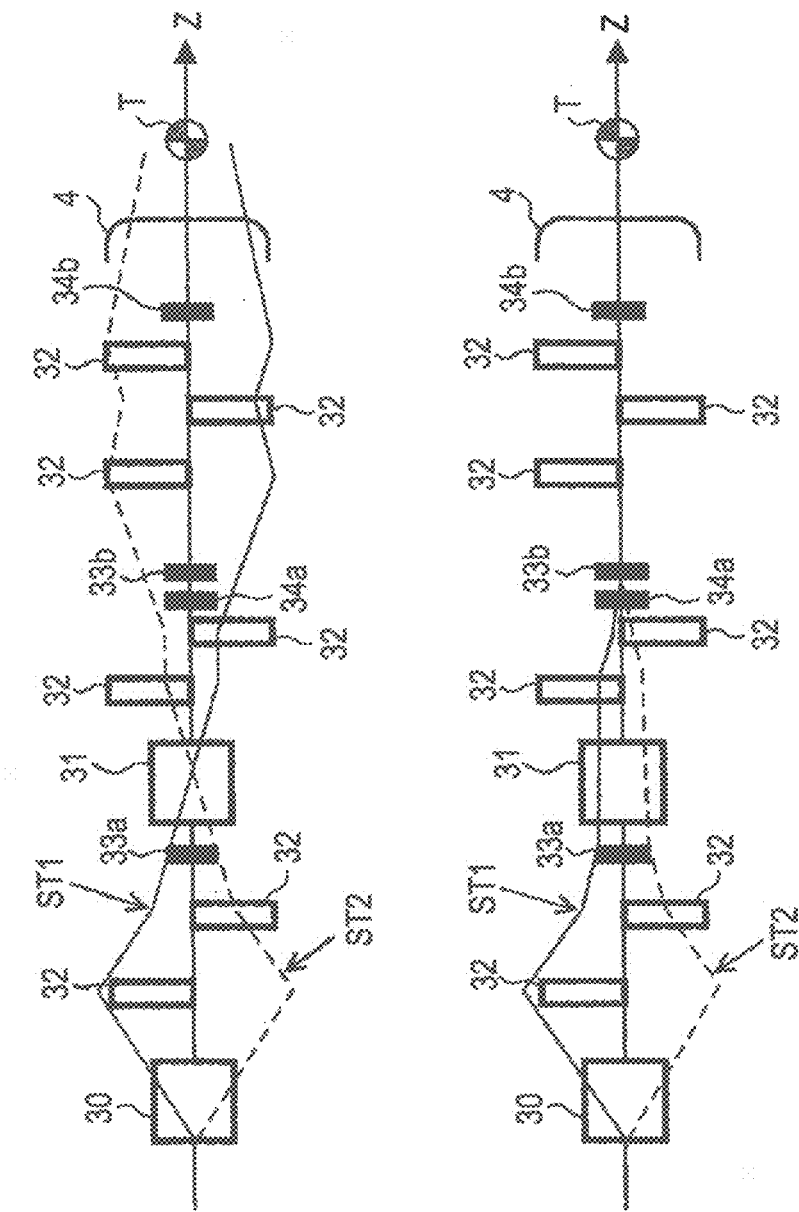
FIGS. 2A and 2B are diagrams schematically illustrating a beam trajectory control state in a beam transport system according to Embodiment 1 of the present invention.

FIG. 2 is a diagram schematically illustrating a beam trajectory control state in the beam transport system 3 according to Embodiment 1 illustrated in FIG. 1, whereby electromagnets correspond to those illustrated in FIG. 1. FIG. 2(a) illustrates a beam trajectory before correcting the beam trajectory according to the present invention and FIG. 2(b) illustrates a beam trajectory representing the beam trajectory correction result according to the present invention. The principle of correcting influences of a beam position variation and a beam angle variation which periodically vary will be described below with reference to the drawing. In the drawing, Z represents an ideal beam axis line traveling to an irradiation location T, ST1 represents a beam trajectory, for example, at time t1, and ST2 represents a beam trajectory at time t2 which is different from time t1.

Figure 3:
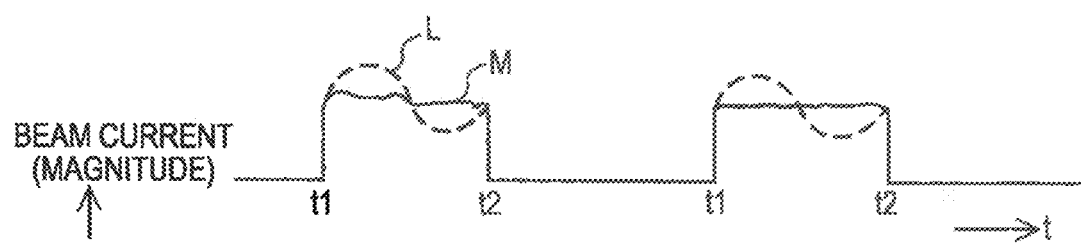
FIG. 3 is a diagram illustrating a temporal variation of a beam current (magnitude) of a charged particle beam emitted to the beam transport system according to Embodiment 1.

FIG. 3 illustrates a temporal variation of a beam current (magnitude) of a charged particle beam emitted to the beam transport system 3 and illustrates a state where a high-energy beam is emitted from the synchrotron 2 to the beam transport system 3 in a period of between t1 and t2 which is referred to as a beam spill, then the emission of a beam is stopped for a predetermined time, and the next emission of a beam is repeated. The length of the beam spill period varies depending on a respiration state or other conditions of a patient, operating conditions of the synchrotron, and the like. In general, a beam trajectory of a beam is adjusted by the use of the deflection electromagnets 31, the four-pole electromagnets 32, and the like depending on the emission conditions, and the beam is guided to an irradiation device and is finally applied to an irradiation object in a predetermined beam axis line z.

However, when there is a periodic variation of a magnetic field of an electromagnet or high-frequency power in the synchrotron at the time of taking out a charged particle beam from the synchrotron 2, the periodic variation L is superimposed on the normal state M of the beam current (magnitude) and they become complicatedly interrelated due to the position variation or the angle variation of the emitted beam. In the conventional correction method using a feedback system, the beam trajectories ST1 and ST2 illustrated in FIG. 2(a) are obtained and thus it is not possible to completely correct the influence of misalignment due to the periodic variation factor.

In Embodiment 1 of the present invention, as illustrated in FIG. 2(b), a beam center is bent to pass through the beam axis line z in the second steering electromagnet 33b using the first steering electromagnet 33a, then the slope of the beam center is caused to be parallel to the beam axis line z using the second steering electromagnet 33b, and then the beam center travels along the beam axis line z.

Accordingly, in order to adjust the first steering electromagnet 33a, the first beam position monitor 34a is disposed in front of the second steering electromagnet 33b and the second beam position monitor 34b is disposed behind the second steering electromagnet 33b, whereby the second steering electromagnet 33b is adjusted.

A specific beam correcting method using the steering electromagnet power supplies 41 and 42 in this embodiment will be described in brief with reference to FIGS. 4 and 5. FIG. 4 is a flowchart illustrating a specific beam correcting procedure and FIG. 5 is a basic conceptual diagram illustrating a method of calculating a kick angle in each steering electromagnet. In FIG. 4, first, in step S1, a detection signal $X1(t)$ indicating a beam position variation at each time t is detected by the first beam position monitor 34a located upstream and is input to the steering electromagnet power supply 41.

Figure 5A:
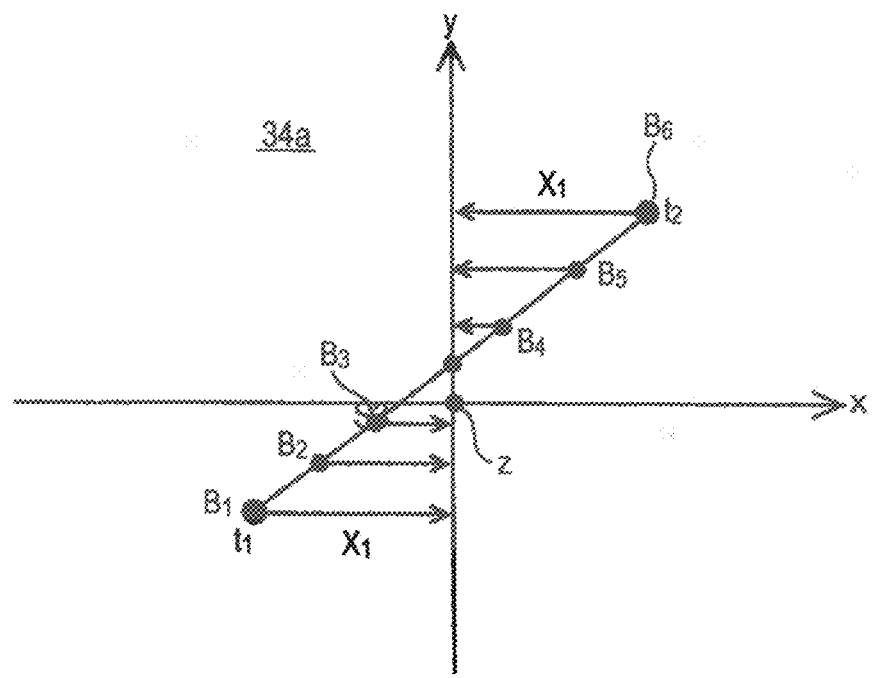
FIGS. 5A and 5B are basic conceptual diagrams illustrating a method of calculating a kick angle in each steering electromagnet.

Time t indicates plural time points in the beam spill period of from t1 to t2 and is for detecting a dynamic variation of a beam position at each time point. FIG. 5(a) illustrates an example of a variation from beam position B1 to beam position B5 when a beam position at time t (from t1 to t2) on the x axis and the y axis which are perpendicular to each other and perpendicular to the z axis is observed using the first beam position monitor 34a with the traveling direction Z of the beam set to a direction perpendicular to the drawing sheet. The beam position has behavior departing from the beam axis z due to the periodic variation factor.

FIG. 5(a) illustrates only x-axis components at the beam positions, but y-axis components are also present.

In step S2, the detection signal X1 of the first beam position monitor 34a is input to the steering electromagnet power supply 41 and the kick angle of the steering electromagnet 33a with X1=0 is calculated at each time therein. In this calculation, empirical values in which the kick angles are correlated with the detection signals X1 are prepared in advance in the form of a time table in the controller of the steering electromagnet power supply 41 and the kick angle of the steering electromagnet 33a with X1=0 is derived depending on X1 at each time.

Subsequently, in step S3, a current pattern $I1(t)$ based on the calculated kick angle is created and stored. Current patterns correlated with the kick angles are prepared in the form of a time table in the controller of the steering electromagnet power supply 41, the current patterns are corrected to linear current patterns $I1(t)$, for example, by performing linear interpolation on the current patterns corresponding to the calculated kick angles, and the linear current patterns are output as an excitation current of the steering electromagnet 33a to correct the beam position.

In step S4, the beam center of the beam trajectory is bent to pass through the beam axis line z in the second steering electromagnet 33b using the current pattern $I1(t)$ as the excitation current of the steering electromagnet 33a, the detection signal $X2(t)$ indicating the beam position variation at time t (from t1 to t2) is detected by the second beam position monitor 34b located downstream, and the detection signal is input to the second steering electromagnet power supply 42 located downstream.

Figure 5B:
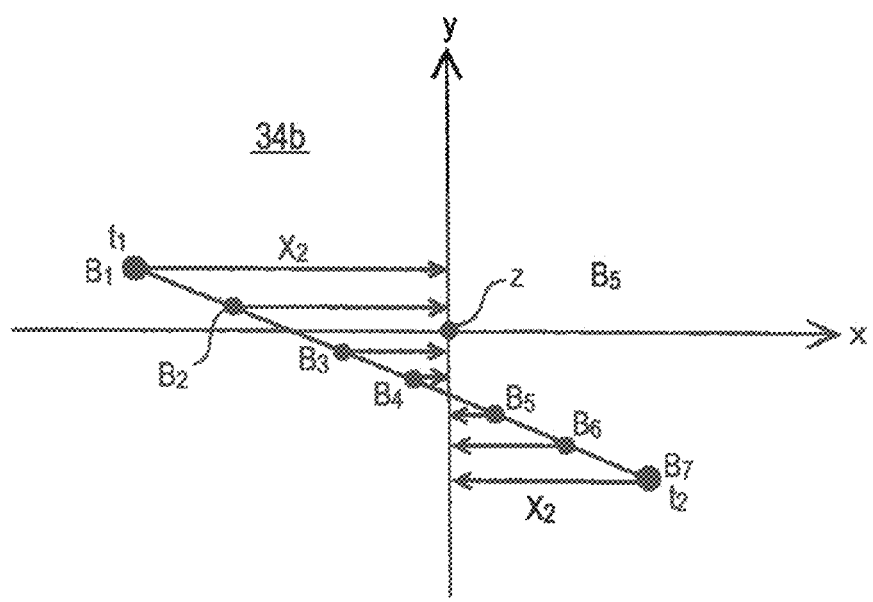

In step S5, the kick angle of the steering electromagnet ST2 at which the detection signal X2 is equal to 0 is calculated by the second steering electromagnet power supply 42. FIG. 5(b) illustrates an example of a variation from beam position B1 to beam position B7 when a beam position at time t (from t1 to t2) on the x axis and the y axis is observed using the second beam position monitor 34b. The beam position B has behavior departing from the beam axis z due to the periodic variation factor. The calculation methods in steps S4 and S5 are the same as in steps S1 and S2.

In step S6, a current pattern $I2(t)$ based on the calculated kick angle is created and stored. Current patterns correlated with the kick angles are prepared in the form of a time table in the controller of the steering electromagnet power supply 42, the current patterns are corrected to linear current patterns $I2(t)$, for example, by performing linear interpolation on the current patterns corresponding to the calculated kick angles. In step S7, the linear current patterns are output as an excitation current of the steering electromagnet 33b to correct the beam position so as to be finally located on the beam axis.

The above description mentions a preliminary operation in test irradiation, and in actual irradiation, a patient is irradiated with a beam to treat the patient in a state where the beam position and the beam angle do not vary by causing the stored current patterns to flow in the upstream steering electromagnet and the downstream steering electromagnet in synchronization with the synchrotron which is periodically operated.

Figure 6:
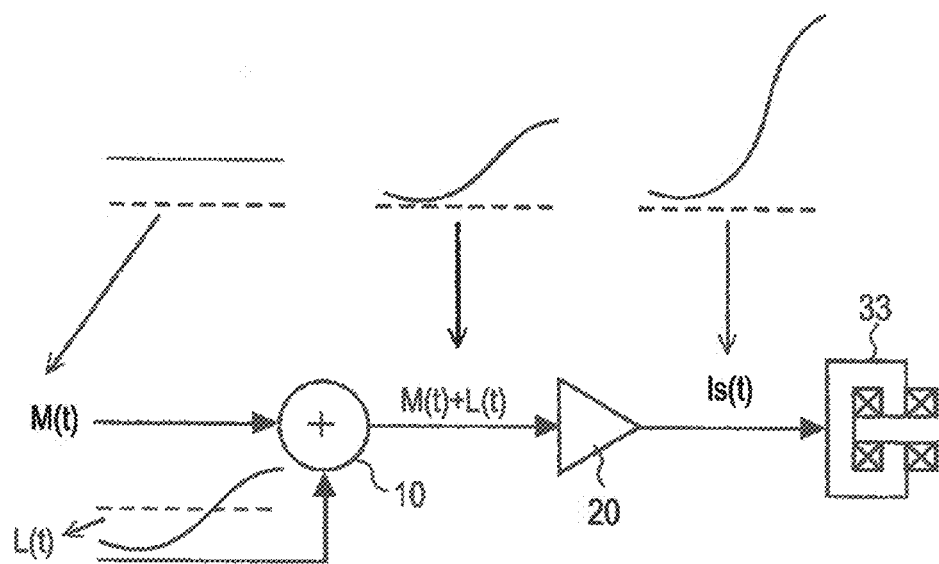

A functional block diagram of the beam trajectory correction control including a corrected current pattern due to the periodic variation factor and a corrected current pattern due to a device arrangement error or the like is illustrated in FIG. 6.

FIG. 6 illustrates an adder 10 that adds a corrected current pattern signal L(t) based on the periodic error variation of devices to a corrected current pattern signal M(t) based on the device arrangement error or the like, a power supply 20 that is able to output a current Is(t) proportional to the added signal, and another steering electromagnet 33 that is able to give a kick to the beam trajectory.

FIG. 7 is a characteristic diagram illustrating a state where the effect of the correction control varies depending on the correction procedure.

FIG. 7(A) is a diagram illustrating beam behavior when the correction using the steering electromagnet is not carried out at all and illustrates an accelerator-emitted beam current in the upper part, the steering electromagnet current Is(t) in the middle part, and the beam position (x(t), y(t)) at an irradiation location in the lower part, which is true of FIGS. 7(B) and 7(C).

In FIG. 7(A), the beam position (x(t), y (t)) (lowest part) at the irradiation location of a beam emitted in synchronization with the periodic operation of the synchrotron includes the irradiation location s and a trajectory variation in which a motion of a DC trajectory due to the device arrangement error and a motion of a periodic trajectory due to a periodic error variation of a device are matched with each other, and is observed by the beam position monitor. There is a periodic variation due to the beam position monitor, but a steering electromagnet current M(t) in which the average of the variations is 0 is acquired by measurement and calculation and is temporarily stored.

FIG. 7(B) is a diagram illustrating beam behavior when correction is carried out using the steering electromagnet current M(t), where the average of the beam position variation (x(t), y(t)) is 0 by causing the steering electromagnet current M(t) acquired in the above procedure to flow therein. The beam position varying between emissions of accelerated beams is observed by the use of the beam position monitor, and a steering electromagnet current L(t) for causing the beam position not to vary is calculated and stored from the observation result.

FIG. 7(C) is a diagram illustrating beam behavior when correction of M(t)+L(t) is carried out, where the variation of the beam position (x(t), y(t)) is 0 by causing the current M(t)+L(t), which is obtained by adding the steering electromagnet current L(t) acquired in the above procedure to M(t), to flow in the steering electromagnet.

Figure 8:
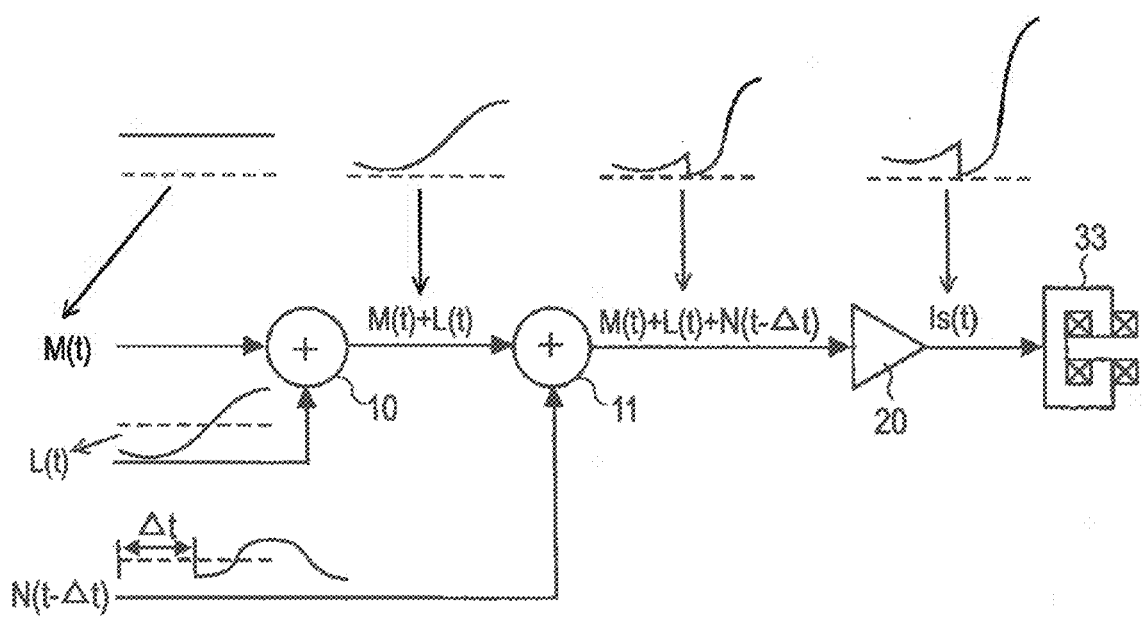
FIG. 8 is a functional block diagram illustrating a beam trajectory correction control state in respiration-synchronized irradiation.

FIG. 8 is a block diagram illustrating a beam trajectory correction control function in respiration-synchronized irradiation. By adding one adder 11 in addition to the adder 10 illustrated in FIG. 6 and further adding a corrected current pattern signal N(t−Δt) based on a respiration-synchronized signal trigger signal (delayed by Δt from the accelerator emission time), a current signal (M(t)+L(t)+N(t−Δt)) capable of correcting a variation of the beam position due to the respiration-synchronized irradiation is made to flow, thereby correcting the beam position variation.

Figure 9A:
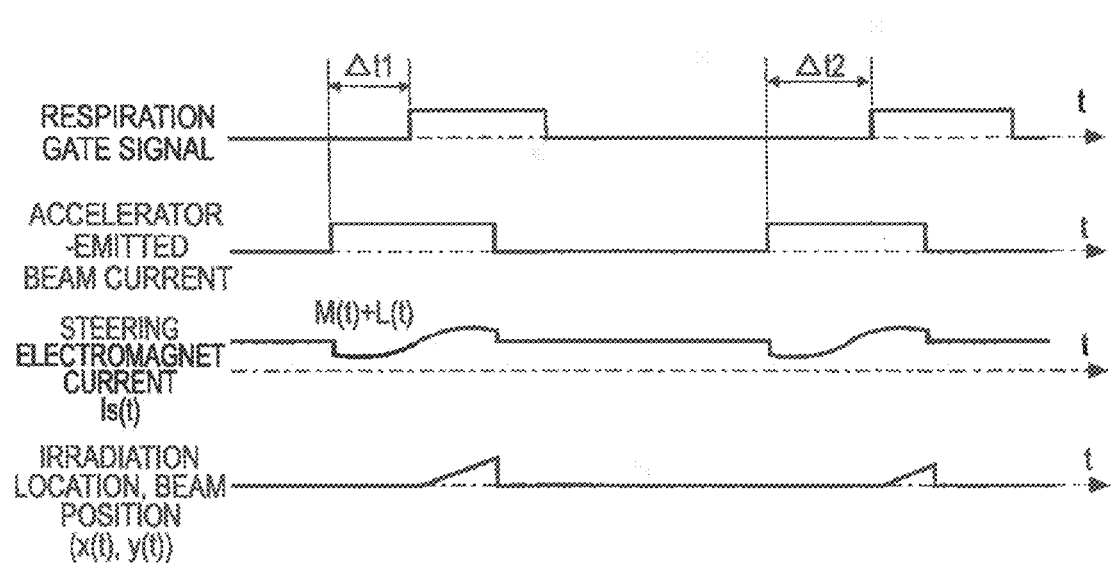
FIGS. 9A and 9B are characteristic diagrams illustrating a case where a beam position variation is corrected in consideration of a position variation due to devices with the respiration-synchronized irradiation.
Figure 9B:
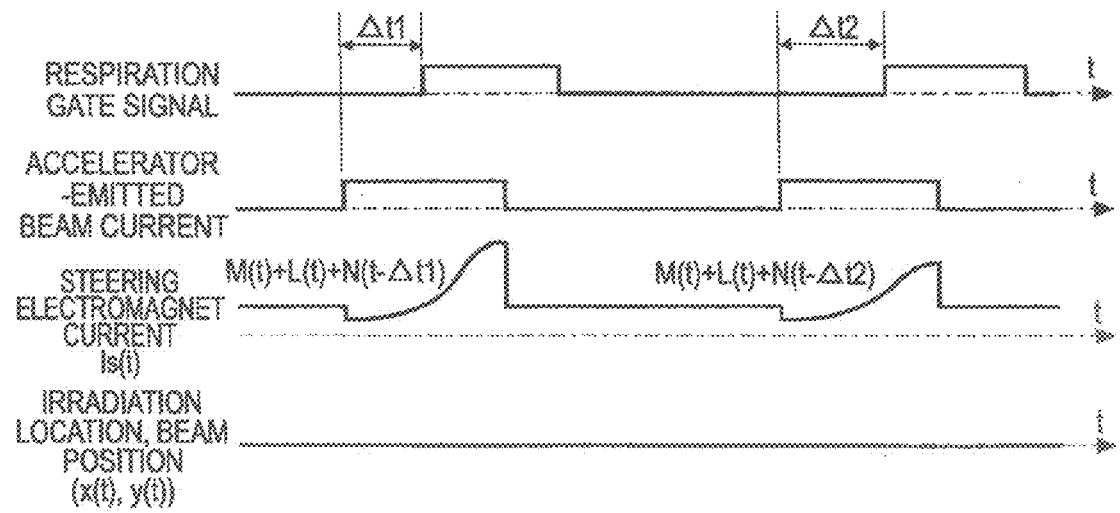

FIG. 9 illustrates a case where a beam position variation is corrected in consideration of a position variation due to a device based on the respiration-synchronized irradiation. FIG. 9(A) illustrates a case where correction is carried out using M(t)+L(t). When a respiration-synchronized irradiation function is used at the time of correction using M(t)+L(t), a variation in the beam position (x(t), y(t)) due to devices based on the respiration-synchronized emission occurs (see the lowest part). When it is assumed that a respiration gate signal is generated with a time delay of Δt from the beam emission, the beam position variation is similarly observed with the beam position monitor under this condition and a current value pattern N(t) not varying is acquired and stored from the observation result. Then, in the actual irradiation, as illustrated in FIG. 9(B), by adding a corrected current N(t−Δt) which is delayed by Δt=Δt1=Δt2, the steering electromagnet current (M(t)+L(t)+N(t−Δt)) is made to flow and the variation of the beam position (x(t), y(t)) can be made to be 0 (see the lowest part).

In FIG. 1, the upstream beam position monitor is disposed in the vicinity of the upstream side of the downstream steering electromagnet. However, since it is ideal that the upstream beam position monitor monitors the beam position at the position of the downstream steering electromagnet but the upstream beam position monitor cannot be disposed in the downstream steering electromagnet, the upstream beam position monitor is disposed in the vicinity of the upstream side of the downstream steering electromagnet. Instead, by providing two upstream beam position monitors, disposing one thereof upstream of the downstream steering electromagnet, and disposing the other thereof downstream of the downstream steering electromagnet, the beam position in the downstream steering electromagnet may be calculated more accurately from the measured values of the two beam position monitors, thereby further improving accuracy of the beam position.

Embodiment 2

A schematic configuration of a particle beam treatment system 100 according to Embodiment 2 of the present invention will be described below with reference to FIG. 10. The particle beam treatment system according to this embodiment has the same system configuration as described in Embodiment 1. Embodiment 1 describes an example where two steering electromagnets and two beam position monitors corresponding thereto are used in the beam transport system 3, but this embodiment is different from Embodiment 1, in that one steering electromagnet 33 and one beam position monitor 34 corresponding thereto are used. The one beam position monitor 34 is disposed at an irradiation position T in test irradiation (preliminary stage).

Figure 10:
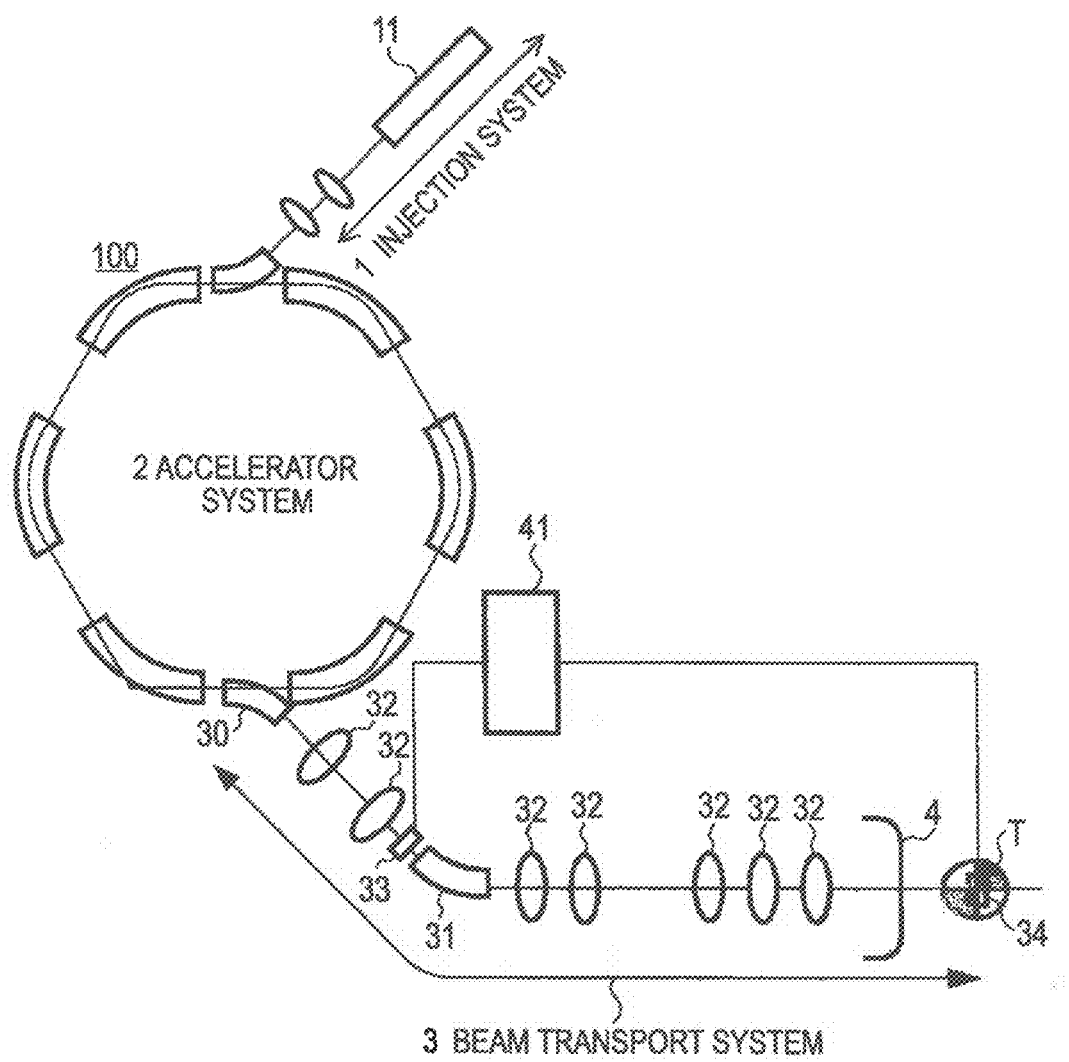
FIG. 10 is a diagram schematically illustrating a configuration of a particle beam treatment system according to Embodiment 2 of the present invention.

FIG. 11 is a diagram schematically illustrating a beam trajectory control state in the preliminary stage, where electromagnets correspond to those illustrated in FIG. 10. FIG. 11(a) illustrates a beam trajectory before correction of the beam trajectory and FIG. 11(b) illustrates a beam trajectory showing the correction result of the beam trajectory. That is, a steering electromagnet current is controlled with respect to time while performing a monitoring operation by the use of the beam position monitor 34, and the steering electromagnet current in a state where the variation of a beam at the irradiation location disappears as a result is detected and stored. Subsequently, in actual irradiation (treatment), the beam position monitor 34 is removed and the kick angle is controlled with respect to time by causing the detected and stored steering electromagnet current to flow.

Figure 12:
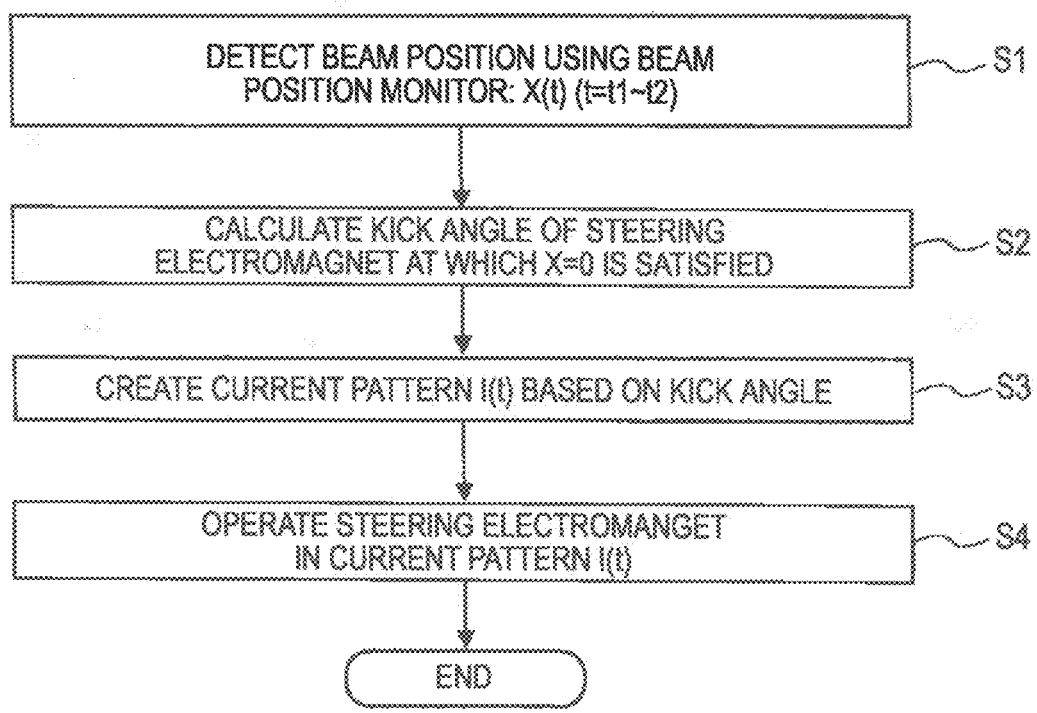
FIG. 12 is a flowchart illustrating a beam correcting procedure using a steering electromagnet power supply in Embodiment 2.

FIG. 12 is a flowchart illustrating a specific beam correcting procedure. In step S1, the beam position monitor 34 positioned at the irradiation location T is operated to cause the beam center of a beam trajectory to pass through the irradiation location T, and a detection signal X(t) indicating a beam position variation at time t (from t1 to t2) is detected and is input to the steering electromagnet power supply 41.

In step S2, the steering electromagnet power supply 41 calculates the kick angle of the steering electromagnet 33 at which the detection signal X is equal to 0.

In step S3, a current pattern I(t) corresponding to the calculated kick angle is created and stored. The current patterns corresponding to the kick angles are prepared in the form of a time table in the controller of the steering electromagnet power supply 41, and the current patterns are corrected to linear current patterns I(t), for example, by performing linear interpolation on the current patterns corresponding to the calculated kick angle. In step S4, the linear current pattern is output as an excitation current of the steering electromagnet 33 and the beam position is corrected to be finally located on the beam axis.

The above description mentions a preliminary operation in test irradiation, and in actual irradiation, a patient is irradiated with a beam to treat the patient in a state where the beam position and the beam angle do not vary by causing the stored current patterns to flow in the steering electromagnet 33 in synchronization with the synchrotron 2 which is periodically operated. Accordingly, it is possible to control the beam trajectory more simply than in the case of Embodiment 1.

Figure 13:
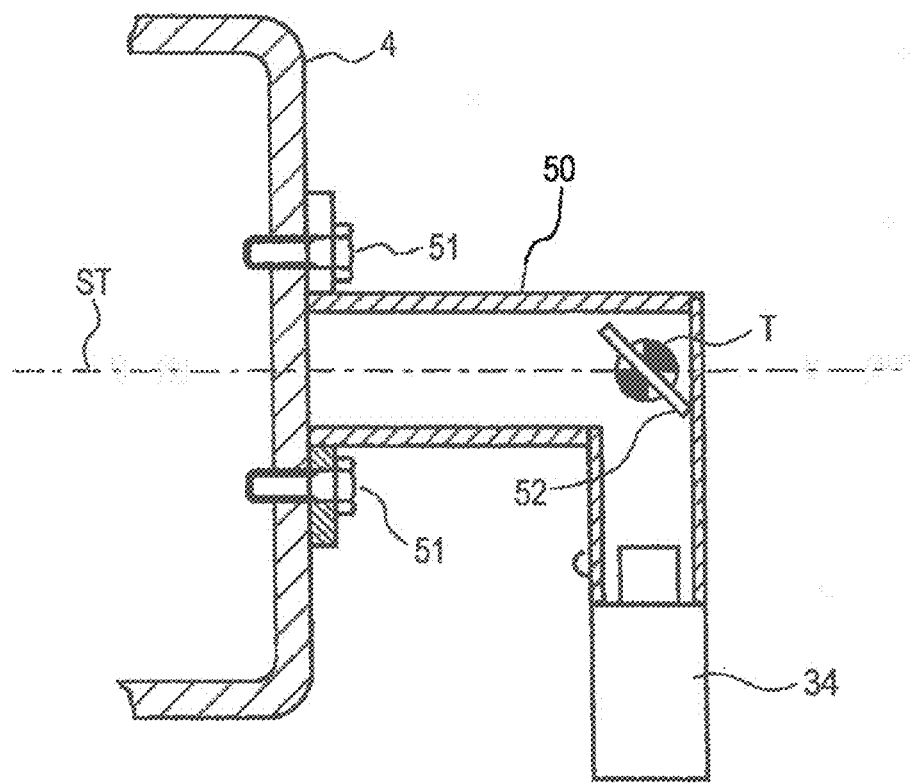
FIG. 13 is a diagram schematically illustrating a configuration of a monitoring device that measures a beam position at an irradiation location.

FIG. 13 is a diagram schematically illustrating a monitor device that measures a beam position at the irradiation location. An attachment 50 having the beam position monitor 34 or the fluorescent plate 52 built therein with fixtures 51 such as bolts and nuts can be detachably attached from the outside of the nozzle 4, and a beam position when a beam trajectory ST is positioned at the irradiation location T can be imaged by the use of the beam position monitor 34 (camera). By using the monitor device that measures a beam position at the irradiation location, the beam position monitor 34 is disposed at the irradiation location T in the test irradiation (preliminary stage), and the beam position monitor 34 is detached using the fixtures 51 in the actual irradiation (treatment).

Embodiment 3

FIG. 14 is a schematic diagram illustrating another beam trajectory control method in the preliminary stage of a particle beam treatment system according to Embodiment 3 of the present invention, where FIG. 14(a) illustrates an example of a beam trajectory when there is no disturbance and FIG. 14(b) illustrates a beam trajectory when there is disturbance. FIG. 14(c) illustrates a correction method according to this embodiment. The same elements as in Embodiments 1 and 2 will not be described and it is assumed that a motion of a beam periodically accelerated and emitted by a synchrotron is observed by the use of the beam position monitor 34 disposed downstream of a deflection electromagnet 31 in the final stage.

The beam trajectory in the beam transport system 3 is calculated from the observation result, and the steering electromagnet 33 is disposed at a position (point A) at which the beam position $X0(s)$ at the position s when there is no disturbance and the beam position $X1(s)$ at the position s when there is disturbance are equal to each other, that is, at the position s at which $X0(s)=X1(s)$ is established, as illustrated in FIG. 14(c). Then, in the test irradiation, a current is caused to flow in the steering electromagnet 33 and a current pattern in which the beam position does not vary is acquired and stored by the use of the beam position monitor 34. In the actual irradiation, a current based on the current pattern is caused to flow so as not to change the beam position and the beam angle.

Embodiment 4

Figure 15A:
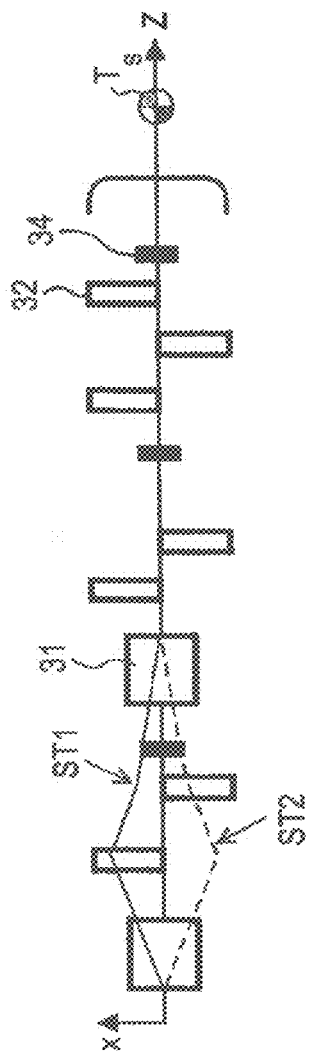
FIGS. 15A to 15C are diagrams schematically illustrating still another beam trajectory control method in the preliminary stage of the particle beam treatment system according to Embodiment 4 of the present invention.
Figure 15B:
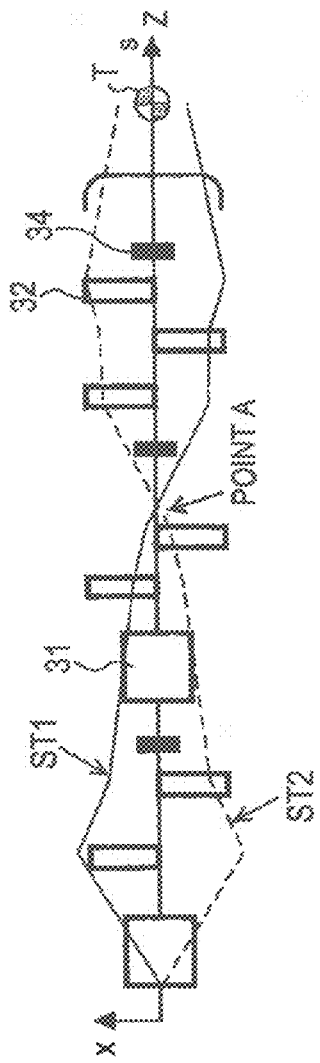

FIG. 15 is a schematic diagram illustrating still another beam trajectory control method in the preliminary stage of a particle beam treatment system according to Embodiment 4 of the present invention, where FIG. 15(a) illustrates an example of a beam trajectory when there is no disturbance and FIG. 15(b) illustrates a beam trajectory when there is disturbance. It is assumed that a motion of a beam periodically accelerated and emitted by a synchrotron is observed by the use of the beam position monitor 34 disposed downstream of the deflection electromagnet 31 in the final stage and disposed behind the four-pole electromagnet 32 in the final stage.

Figure 15C:
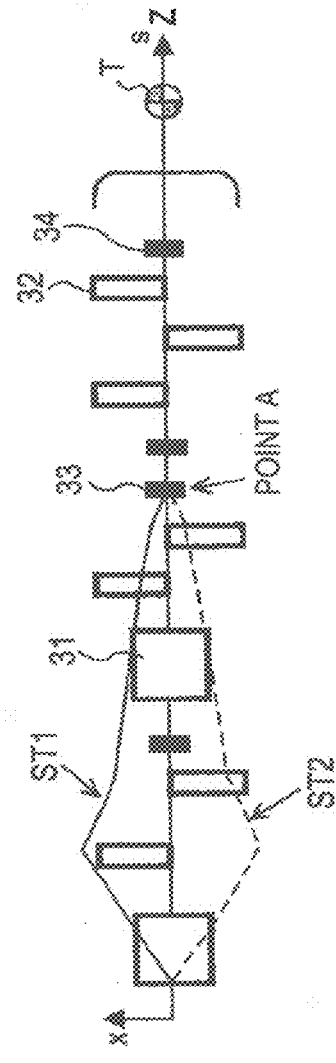

The beam trajectory in the beam transport system 3 is calculated from the observation result, and the steering electromagnet 33 is disposed at a position s (that is, point A at which $X0(s)=X1(s)=0$ is established) at which the beam position $X0(s)$ at the position s when there is no disturbance and the beam position $X1(s)$ at the position s when there is disturbance are equal to each other and are equal to 0 (FIG. 15(c)). Then, in the test irradiation, a current is caused to flow in the steering electromagnet 33 to control the kick angle with respect to time and a current pattern in which the beam position does not vary is acquired and stored by the use of the beam position monitor 34. In the actual irradiation, a current based on the current pattern is caused to flow so as not to change the beam position and the beam angle.

Embodiment 5

A schematic configuration of a particle beam treatment system according to Embodiment 5 of the present invention will be described below with reference to FIG. 16. The particle beam treatment system 100 according to this embodiment basically has the same configuration as in Embodiment 1 illustrated in FIG. 1 and is different from that of Embodiment 1 only in insertion positions of the steering electromagnets 33a and 33b and the beam position monitors 34a and 34b. That is, in Embodiment 1, the first steering electromagnet 33a, the first beam position monitor 34a, the second steering electromagnet 33b, and the second beam position monitor 34b are disposed in this order in the beam transport direction. On the contrary, in this embodiment, the first steering electromagnet 33a, the second steering electromagnet 33b, the first beam position monitor 34a, and the second beam position monitor 34b are disposed in this order.

Figure 16:
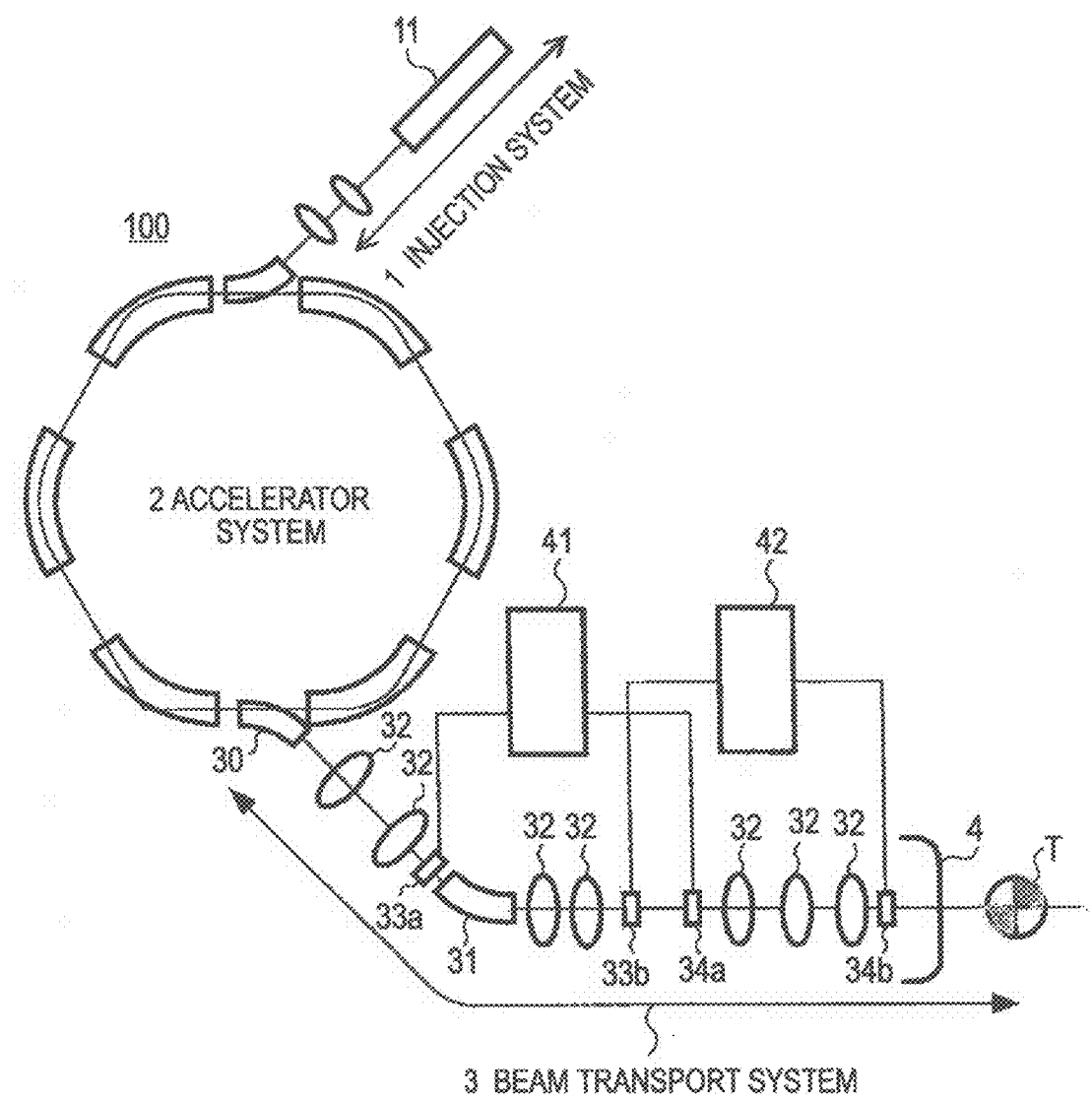
FIG. 16 is a diagram schematically illustrating a configuration of a particle beam treatment system according to Embodiment 5 of the present invention.
Figure 17:
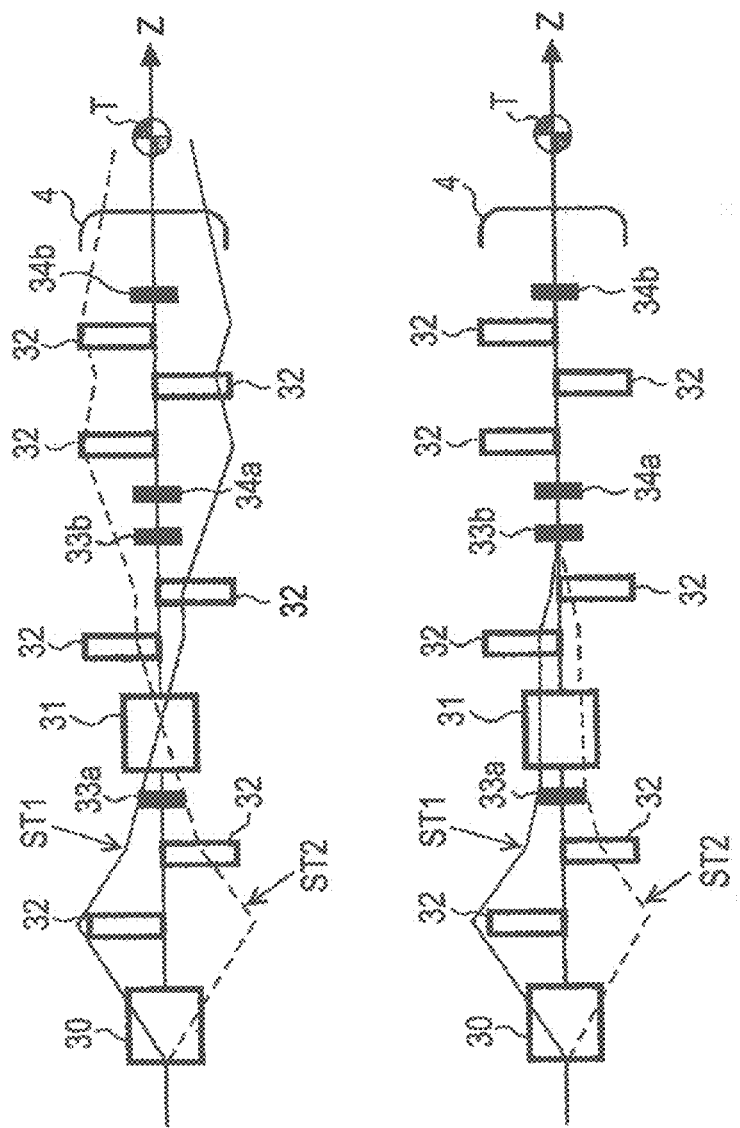
FIGS. 17A and 17B are diagrams schematically illustrating a beam trajectory control state in a beam transport system according to Embodiment 5 of the present invention.

FIG. 17 is a diagram schematically illustrating a beam trajectory control state in the beam transport system 3 according to the embodiment illustrated in FIG. 16, where the electromagnets correspond to those illustrated in FIG. 16. The method of calculating the kick angle in each steering electromagnet is the same as described with reference to FIG. 5 and thus will not be repeatedly described herein.

FIG. 17(a) illustrates a beam trajectory when the control according to the present invention is not carried out and FIG. 17(b) illustrates a beam trajectory when the control according to the present invention is carried out. In the drawings, z represents an ideal beam axis line traveling to the irradiation location T, ST1 represents a beam trajectory at time t1, and ST2 represents a beam trajectory at time t2. Hereinafter, the principle of calculating the kick quantity (angle) of the steering electromagnet for correcting the influence of the beam position variation and the beam angle variation periodically varying using the beam trajectories will be described.

In Embodiment 1 of the present invention, the first beam position monitor 34a and the second beam position monitor 34b are disposed behind (downstream of) the first steering electromagnet 33a and the second steering electromagnet 33b. As illustrated in FIG. 17(b), two steering electromagnets of the first steering electromagnet 33a and the second steering electromagnet 33b are used, the slope of the beam center is bent to be parallel to the beam axis line z by the use of the second steering electromagnet 33b, and then the beam center travels along the beam axis line z.

The reason of requiring at least two steering electromagnets and at least two beam position monitors is that both the position and the slope are able to be corrected to 0.

Figure 18:
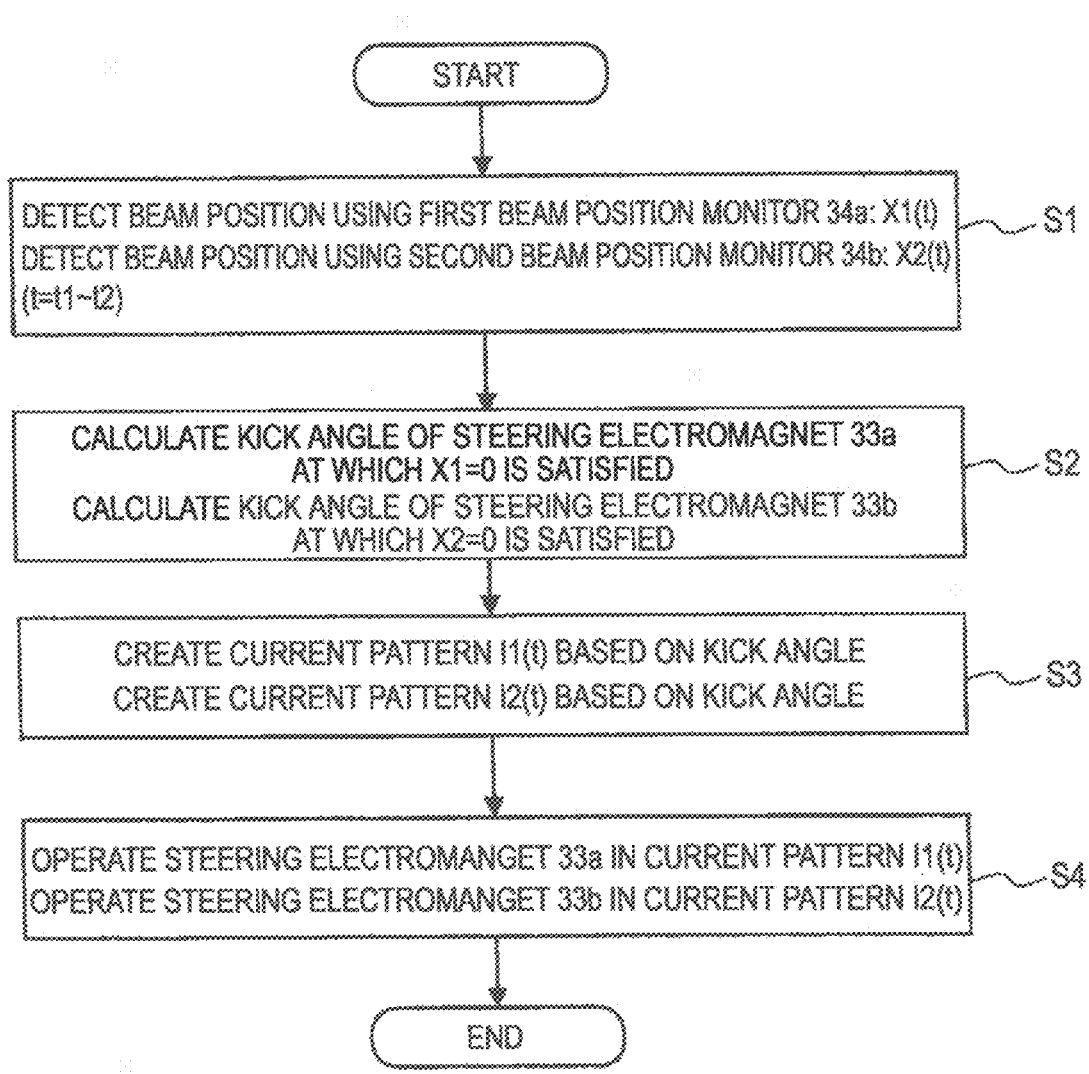
FIG. 18 is a flowchart illustrating a beam correcting procedure using a steering electromagnet power supply in Embodiment 5.

A specific beam correcting method using the steering electromagnet power supplies 41 and 42 according to this embodiment will be described below. FIG. 18 is a flowchart illustrating the specific beam correcting procedure. In the drawing, first, in step S1, the detection signal X1(t) of the beam position at time t is detected by the use of the first beam position monitor 34a, and the detection signal X2(t) of the beam position at time t is detected by the use of the second beam position monitor 34b.

Then, in step S2, the kick angle at each time at which X1 and X2 can be made to zero is calculated by solving simultaneous equations using a calculator (not illustrated) which is an adjustment support terminal or applying a repetition method.

Subsequently, in step S3, current patterns I1(t) and I2(t) corresponding to the calculated kick angle are created. The current patterns corresponding to the kick angles are prepared in the form of a time table in the controllers of the steering electromagnet power supplies 41 and 42, the current patterns are corrected to linear current patterns I1(t) and I2(t), for example, by performing linear interpolation on the current patterns corresponding to the calculated kick angles, and the linear current patterns are output as the excitation currents of the steering electromagnets 33a and 33b to correct the beam position so as to be finally located on the beam axis.

Since the same advantageous effects as in Embodiment 1 are achieved from this embodiment and device arrangement is limited due to constraint conditions such as building arrangement, this embodiment may be more advantageous in some cases.

Embodiment 6

In a particle beam treatment system, plural deflection electromagnets or steering electromagnets for changing a traveling direction of a charged particle beam and plural four-pole electromagnets for controlling a beam width by causing the charged particle beam to converge or diverge are generally disposed in a beam transport system. Therefore, a space for housing the devices is considerably large and a building area sufficient to house the devices is necessary. For example, a large deflection electromagnet has a height of 2.5 m and a deflection radius of 1.5 m, and it may be necessary to provide plural deflection electromagnets depending on the purpose of use. Accordingly, in a variety of equipment in which a large building is not secured, reduction of at least one deflection electromagnet greatly contributes to a decrease in size of the particle beam treatment system and reduces the limitation in arrangement.

Figure 19:
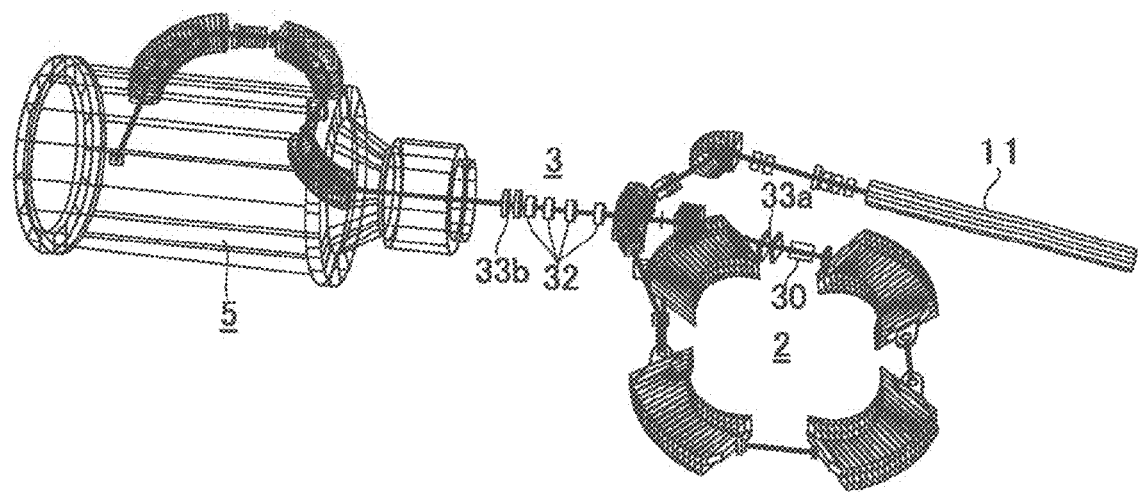
FIG. 19 is a diagram schematically illustrating a configuration of a particle beam treatment system according to Embodiment 6 of the present invention in a state similar to reality.

Embodiment 6 describes that the same purpose is achieved by reducing at least one deflection electromagnet in the beam transport system 3 of the particle beam treatment systems described in Embodiments 1 to 5 and releasing the correlation of the momentum distribution function without using the deflection electromagnet. FIG. 19 is a diagram illustrating a configuration of beam transport system of a particle beam treatment system according to this embodiment.

In the drawing, elements identical or corresponding to those of FIGS. 1 and 10 are referenced by the same reference signs, and reference numeral 5 represents a gantry serving as a treatment room for a patient. In the drawing, a beam emitted from an emitting deflection electromagnet 30 of the accelerator system 2 is illustrated in a state close to reality in the beam transport system 3 up to the gantry 5 by not releasing the correlation of the momentum distribution function by combination of a known four-pole electromagnet and a deflection electromagnet but releasing the correlation of the momentum distribution function by only the four-pole electromagnet 32 and the steering electromagnets 33a and 33b.

Since the momentum distribution function is a correlation function of momentum and position and a charged particle beam emitted from the accelerator system 2 has a correlation of momentum and position, it is important for securing treatment quality to remove the correlation at the time of transporting the beam up to an entrance of the gantry. The beam transport system 3 serves to transport the charged particle beam with the momentum distribution function removed as well as to transport the charged particle beam to the gantry 5. In general, when the momentum distribution is generated in the X direction by the accelerator, a combination of an x-direction deflection electromagnet and a four-pole electromagnet for cancelling the distribution in the x direction is necessary. When a momentum distribution in the y direction is generated by taking out a beam from the accelerator, a combination of a y-direction deflection electromagnet and a four-pole electromagnet for cancelling the distribution in the y direction is necessary.

Various emission methods can be used as the emission method from the accelerator, and there is a method having a property that the time and the momentum distribution are strongly correlated, that is, a tendency that the central momentum greatly varies with the time.

It is considered that this is attributed to a periodic variation of a magnetic field or high-frequency power of an electromagnet in the accelerator, and it is possible to release the periodic variation, that is, the strong correlation of the time and the momentum distribution by monitoring the periodic variation interlocking with the operation cycle of the accelerator by the use of the beam position monitor as described in Embodiments 1 to 5 and correcting the trajectory so as to cancel the dynamic variation of the output of the beam position monitor.

This will be specifically described below with reference to the example illustrated in FIG. 19.

Figure 20A:
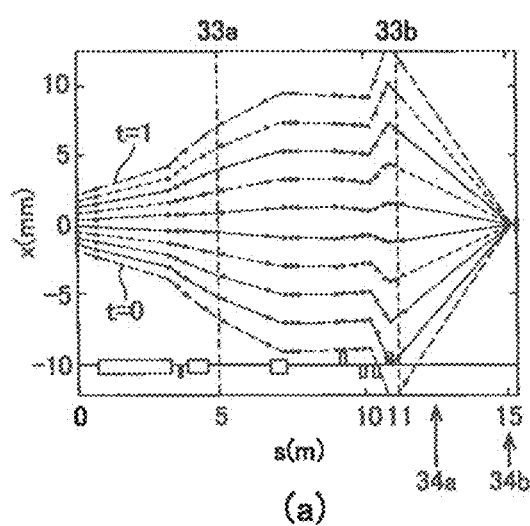
FIGS. 20A and 20B are diagrams illustrating a momentum distribution function of an x axis or a y axis with respect to an axis s along a designed trajectory in the particle beam treatment system according to Embodiment 6 of the present invention.
Figure 20B:
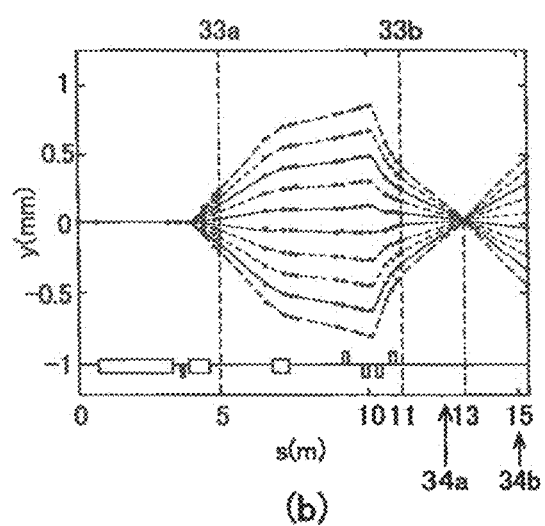

A beam emitted from a synchrotron generally has a momentum distribution function in the x direction and the y direction. FIGS. 20(a) and 20(b) are diagrams illustrating the momentum distribution function (vertical axis) in the x axis or the y axis with respect to the distance (m) of an axis s (horizontal axis) along a designed trajectory, that is, displacements x (mm) and y (mm) from the designed trajectory, and illustrate a state where the momentum distribution function greatly varies with the time. The lower parts of the drawings (t=0) represent the initial emission state and the upper trajectories are followed with the time. In the drawings, time intervals up to t=1 are illustrated. The axis s (m) along the designed trajectory is an example where an exit port of the accelerator system 2 is set to 0 and the distance to the entrance of the gantry 5 is set to 15 m, and large rectangles in the lower parts of the drawings represent the emitting deflection electromagnet 30, a small rectangle of an upper half represents the converging four-pole electromagnet, and a small rectangle of a lower half represents the diverging four-pole electromagnet.

As can be understood from the above description, the time and the momentum have a strong correlation and the momentum of a beam increases with the time. Since a beam hardly moves at a position of s=15 m in the x direction, the momentum distribution function is set to $\eta$=0. However, since the slope varies with the time, a value $\eta'$ obtained by differentiating $\eta$ in the s direction is $\eta'\neq 0$.

On the other hand, since a beam hardly moves at a position of s=13 m in the y direction, $\eta$=0 is set. However, since the slope varies with the time, $\eta'\neq 0$ is established.

In the particle beam treatment system, the momentum distribution function needs to be $\eta$=0 or $\eta'$=0 at the entrance of the rotating gantry or at an isocenter position.

Figure 21A:
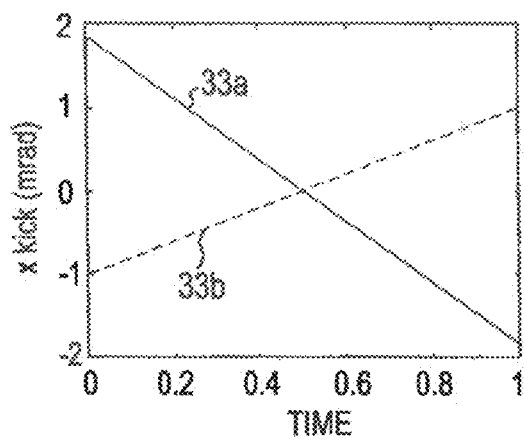
FIGS. 21A and 21B are diagrams illustrating a kick angle for excitation currents to be applied to dynamic steering electromagnets 33a and 33b in Embodiment 6.
Figure 21B:
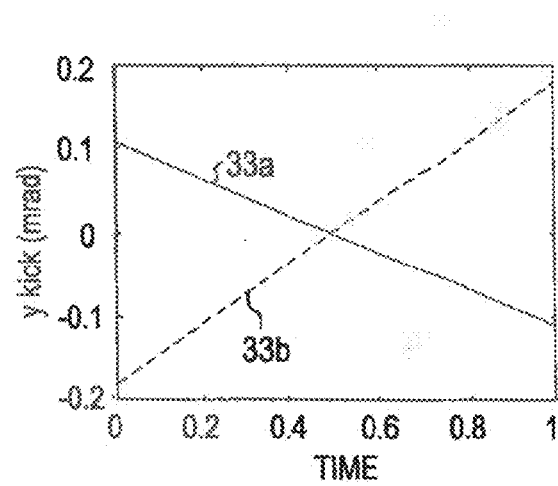
Figure 22A:
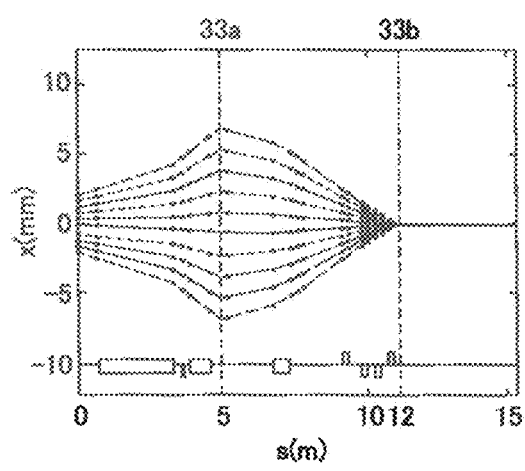
FIGS. 22A and 22B are diagrams illustrating a momentum distribution function obtained by performing control according to Embodiment 6 of the present invention.
Figure 22B:
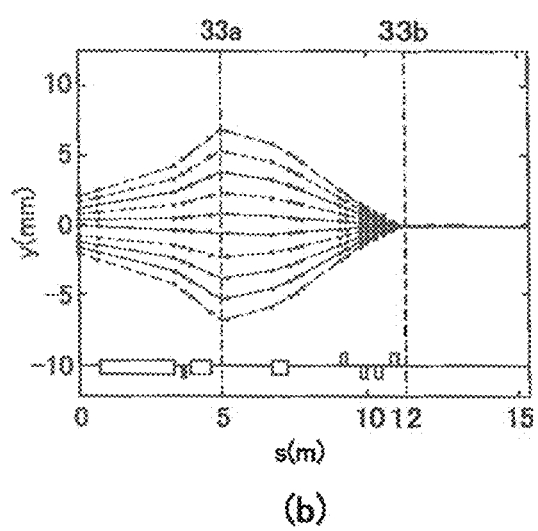

Therefore, two sets of combinations of the steering electromagnets 33a and 33b in the x direction and the y direction are disposed at the position of s=5 m and the position of s=11 m, and the monitors 34a and 34b are disposed, for example, at the position of s=12 m and the position of s=15 m. Here, a current pattern of a dynamic steering electromagnet in which the displacement of the beam center of gravity at the positions of the monitors 34a and 34b is 0 can be acquired using the principle of correcting the variations in beam position and beam angle periodically varying, which is described in Embodiment 5. For example, when it is assumed that the dynamic steering electromagnets 33a and 33b are excited with the current pattern illustrated in FIG. 21, the momentum distribution function illustrated in FIG. 22 is obtained. That is, it was found that x(t)=0, x'(t)=0, y(t)=0, and y'(t)=0 can be realized at the entrance of the gantry. Since the time and the momentum have a strong correlation, $\eta$x=0, $\eta'$x=0, $\eta$y=0, and $\eta'$y=0 are also realized.

When the time and the momentum have a strong correlation in this way, it is possible to reduce the number of deflection electromagnets in comparison with the conventional combination of the deflection electromagnets and the four-pole electromagnets by combining the monitors and the dynamic steering electromagnets, and it is possible to implement a transport path in which the momentum distribution function is 0 by the use of small and low-cost devices.

REFERENCE SIGNS LIST

1: injection system
2: accelerator system
3: beam transport system
4: nozzle
5: gantry
10: adder
11: injector
20: power supply
30, 31: deflection electromagnet
32: four-pole electromagnet
33, 33a, 33b: steering electromagnet
34, 34a, 34b: beam position monitor
41, 42: steering electromagnet power supply
100: particle beam treatment system

The invention claimed is:

1. A particle beam treatment system comprising:
an accelerator system that accelerates a charged particle beam; and
a beam transport system that transports a high-energy beam emitted from an accelerator to an irradiation location,
wherein the beam transport system is provided with two steering electromagnets and two beam position monitors corresponding to the steering electromagnets,
wherein the first beam position monitor is disposed in the front of the second steering electromagnet and is configured to detect beam position variation over a period of time and to supply a first excitation current for correcting a periodic position variation and a periodic angle variation of the beam position based upon the beam position variation detected by the first beam position monitor, to the first steering electromagnet, and
wherein the second beam position monitor is disposed in the back of the second steering electromagnet and is configured to detect beam position variation over the period of time and supply a second excitation current for correcting a periodic position variation and a periodic angle variation of the beam position based upon the beam position variation detected by the second beam position monitor, to the second steering electromagnet.

2. The particle beam treatment system according to claim 1, wherein the first beam position monitor is disposed in the vicinity of the front of the second steering electromagnet and a third beam position monitor is disposed in the vicinity of the back of the second steering electromagnet, and
wherein a position of the second steering electromagnet is calculated from values measured by the first and third beam position monitors.

3. A beam position correcting method of a particle beam treatment system which includes an accelerator system that accelerates a charged particle beam and a beam transport system that transports a high-energy beam emitted from an accelerator to an irradiation location and in which the beam transport system is provided with at least one steering electromagnet and at least one beam position monitor corresponding to the at least one steering electromagnet, comprising:
detecting a periodic variation of a beam position by applying a beam in a state where the at least one beam position monitor is detachably disposed at an irradiation location in test irradiation;
supplying a value of an excitation current to the at least one steering electromagnet in synchronization with the periodic position variation so as to cancel the periodic variation;
storing a value of the periodic excitation current; and
supplying the stored value of the periodic excitation current to the at least one steering electromagnet in a state where the at least one beam position monitor is detached from the irradiation location in actual irradiation.

4. A beam position correcting method of a particle beam treatment system which includes an accelerator system that accelerates a charged particle beam and a beam transport system that transports a high-energy beam emitted from an accelerator to an irradiation location, comprising:
observing a position variation of a beam periodically accelerated and emitted by a synchrotron by the use of a beam position monitor disposed downstream of a deflection electromagnet in a final stage of the beam transport system;
calculating a beam trajectory of the beam transport system on the basis of the observation result, wherein said calculating takes into account a periodic variation of the beam position;
disposing a steering electromagnet at a position s at which a beam position $X0(s)$ at the position s when there is no disturbance and a beam position $X1(s)$ at the position s when there is disturbance are equal to each other, that is, the position at which $X0(s)=X1(s)$ is satisfied, acquiring and storing a current pattern in which a beam position does not vary by the use of the beam position monitor by causing a current to flow in the steering electromagnet in test irradiation; and causing the beam position and a beam angle not to vary by causing a current corresponding to the current pattern to flow in actual irradiation.

5. The beam position correcting method of a particle beam treatment system according to claim 4, wherein the steering electromagnet is disposed at the position s at which the beam position $X0(s)$ at the position s when there is no disturbance and the beam position $X1(s)$ at the position s when there is disturbance are equal to zero, that is, the position at which $X0(s)=X1(s)=0$ is satisfied.

6. A beam position correcting method of a particle beam treatment system which includes an accelerator system that accelerates a charged particle beam and a beam transport system that transports a high-energy beam emitted from an accelerator to an irradiation location and in which the beam transport system is provided with two steering electromagnets and two beam position monitors disposed in the back of the two steering electromagnets, comprising:

detecting a detection signal $X1(t)$ of a beam position at each time t by the use of the first beam position monitor;

detecting a detection signal $X2(t)$ of the beam position at each time t by the use of the second beam position monitor;

calculating a kick angle at each time at which X1 and X2 are able to be set to 0;

creating current patterns 11(t) and 12(t) corresponding to the calculated kick angle;

outputting the current patterns as excitation currents of the two steering electromagnets, respectively; and correcting the beam position so as to be finally located on a beam axis.

7. A beam position correcting method of a particle beam treatment system, wherein the particle beam treatment system comprises an accelerator system that accelerates a charged particle beam and a beam transport system that transports a high-energy beam emitted from an accelerator to an irradiation location, wherein the beam transport system comprises (i) an upstream steering electromagnet and a downstream steering electromagnet and (ii) an upstream beam position monitor disposed between the upstream steering electromagnet and the downstream steering electromagnet and a downstream beam position monitor positioned downstream of the downstream steering electromagnet, the method comprising:

conducting a test irradiation, comprising the steps of storing current pattern data of the upstream steering electromagnet in which a beam position does not temporally vary, adjusting a current supplied to the upstream steering electromagnet in accordance with the stored current pattern, observing the beam position by the downstream beam position monitor while the adjusted current is supplied to the upstream steering electromagnet, varying the current in the downstream electromagnet, storing current pattern data of the downstream steering electromagnet in which the beam position does not temporally vary; and conducting an actual irradiation, wherein the beam position and beam angle are corrected for temporal variation by supplying current to the upstream steering electromagnet and the downstream steering electromagnet in accordance with the respective stored current patterns, in synchronism with the beam spill period of a synchrotron.

8. The beam position correcting method of a particle beam treatment system according to claim 7, wherein the current pattern data supplied to the downstream steering electromagnet comprises a correction current pattern signal including a periodic error variation of devices and/or a periodic error variation due to devices based on a respiration-synchronized signal.

* * * * *